(12) United States Patent
Yin et al.

(10) Patent No.: US 11,913,056 B2
(45) Date of Patent: Feb. 27, 2024

(54) ENGINEERED MICROORGANISMS EXPRESSING ACETOACETYL-COA REDUCTASE VARIANTS AND METHOD FOR IMPROVING THE YIELD OF PHA

(71) Applicant: SHENZHEN BLUEPHA BIOSCIENCES CO., LTD., Guangdong (CN)

(72) Inventors: Jin Yin, Guangdong (CN); Yu Wang, Guangdong (CN); Xiaocui Xie, Guangdong (CN); Huayu Zhang, Guangdong (CN); Yakun Wu, Guangdong (CN); Tian Liu, Guangdong (CN); Pingan Tang, Guangdong (CN)

(73) Assignee: SHENZHEN BLUEPHA BIOSCIENCES CO., LTD. (CN)

( * ) Notice: Subject to any disclaimer, the term of this patent is extended or adjusted under 35 U.S.C. 154(b) by 0 days.

(21) Appl. No.: 18/031,545

(22) PCT Filed: Jun. 28, 2022

(86) PCT No.: PCT/CN2022/101802
§ 371 (c)(1),
(2) Date: Apr. 12, 2023

(87) PCT Pub. No.: WO2023/193353
PCT Pub. Date: Oct. 12, 2023

(65) Prior Publication Data
US 2023/0323411 A1  Oct. 12, 2023

(51) Int. Cl.
*C12P 7/625* (2022.01)
*C12N 9/04* (2006.01)
*C12N 9/10* (2006.01)
*C12N 9/88* (2006.01)
*C12N 15/74* (2006.01)
*C12N 1/21* (2006.01)

(52) U.S. Cl.
CPC ............ *C12P 7/625* (2013.01); *C12N 9/0006* (2013.01); *C12N 9/1029* (2013.01); *C12N 9/88* (2013.01); *C12N 15/74* (2013.01); *C12Y 101/01036* (2013.01); *C12Y 402/01017* (2013.01)

(58) Field of Classification Search
None
See application file for complete search history.

(56) References Cited

U.S. PATENT DOCUMENTS

2013/0017583 A1   1/2013  Budde et al.

FOREIGN PATENT DOCUMENTS

| CN | 107418960 A | 12/2017 |
|---|---|---|
| CN | 112899316 A | 6/2021 |
| CN | 113322220 A | 8/2021 |
| WO | 2014032633 A1 | 3/2014 |

OTHER PUBLICATIONS

First Office Action for corresponding Chinese application No. 202210353439.7; dated May 26, 2022 (29 pages).
Bian, Shixiang, et al. "Research and Development on the Biosynthesis of Polyhydroxyalkanoate (PHA) ." Advances in New and Renewable Energy 4.6 (2016): 436-442. English Abstract.
Budde, Charles F., et al. "Roles of Multiple Acetoacetyl Coenzyme A Reductases in Polyhydroxybutyrate Biosynthesis in Ralstonia eutropha H16." Journal of Bacteriology 192.20 (2010): 5319-5328.
Budde, Charles F., et al. "Production of Poly(3-Hydroxybutyrate-co-3-Hydroxyhexanoate) from Plant Oil by Engineered Ralstonia eutropha Strains." Applied and Environmental Microbiology 77.9 (2011): 2847-2854.
Chen, Jingyu, et al. "Biosynthesis and Characterization of Polyhydroxyalkanoate Copolyesters in Ralstonia eutropha PHB-4 Harboring a Low-Substrate-Specificity PHA Synthase PhaC2Ps from Pseudomonas stutzeri 1317." Chinese Journal of Chemical Engineering 15.3 (2007): 391-396. English Abstract.
Chen, Xy, et al. "Thirty years of metabolic engineering for biosynthesis of polyhydroxyalkanoates." Chinese Journal of Biotechnology 37.5 (2021): 1794-1811. English Abstract.
Matsumoto, Ken'ichiro, et al. "Directed evolution and structural analysis of NADPH-dependent acetoacetyl coenzyme A (acetoacetyl-CoA) reductase from Ralstonia eutropha reveals two mutations responsible for enhanced kinetics." Applied and Environmental Microbiology 79.19 (2013): 6134-6139.
Sudesh, Kumar, et al. "Synthesis of polyhydroxyalkanoate from palm oil and some new applications." Applied Microbiology and Biotechnology 89 (2011): 1373-1386.
Zhang, Mengxiao, et al. "Modification of acetoacetyl-CoA reduction step in Ralstonia eutropha for biosynthesis of poly (3-hydroxybutyrate-co-3-hydroxyhexanoate) from structurally unrelated compoundss." Microbial Cell Factories 18.1 (2019): 1-12.

(Continued)

*Primary Examiner* — Todd M Epstein
(74) *Attorney, Agent, or Firm* — Mendelsohn Dunleavy, P.C.

(57) ABSTRACT

Provided is engineered microorganisms expressing acetoacetyl-CoA reductase variants and a method for improving the yield of PHA. Compared with the wild-type acetoacetyl-CoA reductase represented by SEQ ID NO. 31, the variant has one or more of the following mutations: (1) mutation of valine at position 141 to isoleucine or leucine; (2) mutation of methionine at position 12 to threonine, serine, alanine, leucine, lysine or isoleucine; (3) mutation of isoleucine at position 194 to valine, leucine or methionine; (4) mutation of glutamic acid at position 42 to lysine, glutamine, leucine, aspartic acid, proline, threonine, asparagine, or histidine; and (5) mutation of phenylalanine at position 55 to valine, alanine or isoleucine. The variants and their coding genes can promote the synthesis and accumulation of PHA by the strain and increase the yield of PHA.

5 Claims, No Drawings
Specification includes a Sequence Listing.

(56) References Cited

OTHER PUBLICATIONS

"Acetoacetyl-CoA reductase [Rudaea cellulosilytica]." National Center for Biotechnology Information, Genbank Accession No. WP_018973707; URL: <https://www.ncbi.nlm.nih.gov/protein/WP_018973707> (2019): 1 pages.

Yaobin, Ren, et al. "The study on polyhydroxyalkanoate and its modification." China Synthetic Resin and Plastics 18.6 (2001): 35-45. English Abstract.

SEQUENCE LISTING

```
<160> NUMBER OF SEQ ID NOS: 52

<210> SEQ ID NO 1
<211> LENGTH: 4235
<212> TYPE: DNA
<213> ORGANISM: Artificial Sequence
<220> FEATURE:
<223> OTHER INFORMATION: pKO C sequence

<400> SEQUENCE: 1
gtgacgcttg catgagtgcc ggcgtgcgtc atgcacggcg ccggcaggcc tgcaggttcc      60
ctcccgtttc cattgaaagg actacacaat gactgacgtt gtcatcgtat ccgccgcccg     120
caccgcggtc ggcaagtttg gcggctcgct ggccaagatc ccggcaccgg aactgggtgc     180
cgtggtcatc aaggccgcgc tggagcgcgc cggcgtcaag ccggagcagg tgagcgaagt     240
catcatgggc caggtgctga ccgccggttc gggccagaac cccgcacgcc aggccgcgat     300
caaggccggc ctgccggcga tggtgccggc catgaccatc aacaaggtgt gcggctcggg     360
cctgaaggcc gtgatgctgg ccgccaacgc gatcatggcg ggcgacgccg agatcgtggt     420
ggccggcggc caggaaaaca tgagcgccgc cccgcacgtg ctgccgggct cgcgcgatgg     480
tttccgcatg ggcgatgcca agctggtcga caccatgcac cgctcgtcac atcctgttgc     540
gttcactgga atcccagtat agactttgac ctgcgagcaa gctgtcaccg gatgtgcttt     600
ccggtctgat gagtccgtga ggacgaaaca gcctctacaa ataattttgt ttaatgtggt     660
tatgtgcgtt aaggaggttt aacgatgcgt aaaggcgaag agctgttcac tggtgtcgtc     720
```

```
cctattctgg tggaactgga tggtgatgtc aacggtcata agttttccgt gcgtggcgag      780
ggtgaaggtg acgcaactaa tggtaaactg acgctgaagt tcatctgtac tactggtaaa      840
ctgccggtac cttggccgac tctggtaacg acgctgactt atggtgttca gtgcttttgct     900
cgttatccga accatatgaa gcagcatgac ttcttcaagt ccgccatgcc ggaaggctat      960
gtgcaggaac gcacgatttc ctttaaggat gacggcacgt acaaaacgcg tgcggaagtg     1020
aaatttgaag gcgataccct ggtaaaccgc attgagctga aaggcattga ctttaaagaa     1080
gacggcaata tcctgggcca taagctggaa tacaatttta acagccacaa tgtttacatc     1140
accgccgata acaaaaaaaa tggcattaaa gcgaatttta aaattcgcca caacgtggag     1200
gatggcagcg tgcagctggc tgatcactac cagcaaaaca ctccaatcgg tgatggtcct     1260
gttctgctgc cagacaatca ctatctgagc acgcaaagcg ttctgtctaa agatccgaac     1320
gagaaacgcg atcatatggt tctgctggag ttcgtaaccg cagcgggcat cacgcatggt     1380
atggatgaac tgtacaaata atcgtcactc caccggtgct acgaggccct ttcgtcttca     1440
agaattctca tgtttgacag cttatcatcg ataagcttta atgcggtagt ttatcacagt     1500
taaattgcta acgcagtcag gcaccgtgta tgaaatctaa caatgcgctc atcgtcatcc     1560
tcggcaccgt caccctggat gctgtaggca taggcttggt tatgccggta ctgccgggcc     1620
tcttgcggga tatcgtccat tccgacagca tcgccagtca ctatgcgtg ctgctagcgc      1680
tatatgcgtt gatgcaattt ctatgcgcac ccgttctcgg agcactgtcc gaccgctttg     1740
gccgccgccc agtcctgctc gcttcgctac ttggagccac tatcgactac gcgatcatgg     1800
cgaccacacc cgtcctgtgg atcctctacg ccggacgcat cgtggccggc atcaccggcg     1860
ccacaggtgc ggttgctggc gcctatatcg ccgacatcac cgatggggaa gatcgggctc     1920
gccacttcgg gctcatgagc gcttgtttcg cgtgggtat ggtggcaggc cccgtggccg      1980
ggggactgtt gggcgccatc tccttgcatg caccattcct tgcggcggcg gtgctcaacg     2040
gcctcaaccct actactgggc tgcttcctaa tgcaggagtc gcataaggga gagcgtcgac     2100
cgatgccctt gagagccttc aacccagtca gctccttccg gtgggcgcgg ggcatgacta     2160
tcgtcgccgc acttatgact gtcttctttta tcatgcaact cgtaggacag gtgccggcag     2220
cgctctgggt cattttcggc gaggaccgct ttcgctggag cgcgacgatg atcggcctgt     2280
cgcttgcggt attcggaatc ttgcacgccc tcgctcaagc cttcgtcact ggtcccgcca     2340
ccaaacgttt cggcgagaag caggccatta tcgccggcat ggcggccgac gcgctgggct     2400
acgtcttgct ggcgttcgcg acgcgaggct ggatggcctt ccccattatg attcttctcg     2460
cttccggcgg catcgggatg cccgcgttgc aggccatgct gtccaggcag gtagatgacg     2520
accatcaggg acagcttcaa ggatcgctcg cggctcttac cagcctaact tcgatcactg     2580
gaccgctgat cgtcacggcg atttatgccg cctcggcgag cacatggaac gggttggcat     2640
ggattgtagg cgccgcccta taccttgtct gcctccccgc gttgcgtcgc ggtgcatgga     2700
gccgggccac ctcgacctga atggaagccg gcggcacctc gctaacggat tcaccactcc     2760
aagaattgga gccaatcaat ttgacttttg tccttttccg ctgcataacc ctgcttcggg     2820
gtcattatag cgattttttc ggtatatcca tcctttttcg cacgatatac aggattttgc     2880
caaagggttc gtgtagactt tccttggtgt atccaacggc gtcagccggg caggataggt     2940
gaagtaggcc cacccgcgag cgggtgttcc ttcttcactg tcccttattc gcacctggcg     3000
gtgctcaacg ggaatcctgc tctgcgaggc tggccgtagg ccggccgcga tgcaggtggc     3060
```

```
tgctgaaccc ccagccggaa ctgaccccac aaggcccaag atccgcagtt caacctgttg      3120
atagtacgta ctaagctctc atgtttcacg tactaagctc tcatgtttaa cgtactaagc      3180
tctcatgttt aacgaactaa accctcatgg ctaacgtact aagctctcat ggctaacgta      3240
ctaagctctc atgtttcacg tactaagctc tcatgtttga acaataaaat taatataaat      3300
cagcaactta aatagcctct aaggttttaa gttttataag aaaaaaaaga atatataagg      3360
cttttaaagc ttttaaggtt taacggttgt ggacaacaag ccaggatgt aacgcactga      3420 gaagcccctta gagcctctca aagcaatttt gagtgacaca ggaacactta acggctgaca      3480
tggattaccc tgttatccct aattaccctg ttatccctaa ttaccctgtt atccctaatt      3540
accctgttat ccctaattac cctgttatcc ctaattaccc tgttatccct aattaccctg      3600
ttatccctaa ttaccctgtt atccctatgg tacccggcca agtctgcggg cgtgcccatg      3660
atgtagagca ccagcgccac cggcgccatg ccatacatca ggaaggtggc aacgcctgcc      3720
accacgttgt gctcggtgat cgccatcatc agcgccacgt agagccagcc aatggccacg      3780
atgtacatca aaaattcatc cttctcgcct atgctctggg gcctcggcag atgcgagcgc      3840
tgcataccgt ccggtaggtc gggaagcgtg cagtgccgag gcggattccc gcattgacag      3900
cgcgtgcgtt gcaaggcaac aatggactca atgtctcgg aatcgctgac gattcccagg      3960
tttctccggc aagcatagcg catggcgtct ccatgcgaga atgtcgcgct gccggataa       4020 aagggagcc gctatcggaa tggacgcaag ccacggccgc agcaggtgcg gtcgagggct      4080
tccagccagt tccagggcag atgtgccggc agaccctccc gctttggggg aggcgcaagc      4140
cgggtccatt cggatagcat ctccccatgc aaagtgccgg ccagggcaat gcccggagcc      4200
ggttcgaata gtgacggcag agagacaatc aaatc                                4235

<210> SEQ ID NO 2
<211> LENGTH: 2887
<212> TYPE: DNA
<213> ORGANISM: Artificial Sequence
<220> FEATURE:
<223> OTHER INFORMATION: pha C gene

<400> SEQUENCE: 2
cgggcgtgcc catgatgtag agcaccagcg ccaccggcgc catgccatac atcaggaagg       60
tggcaacgcc tgccaccacg ttgtgctcgg tgatcgccat catcagcgcc acgtagagcc      120
agccaatggc cacgatgtac atcaaaaatt catccttctc gcctatgctc tggggcctcg      180
gcagatgcga gcgctgcata ccgtccggta ggtcgggaag cgtgcagtgc cgaggcggat      240
tcccgcattg acagcgcgtg cgttgcaagg caacaatgga ctcaaatgtc tcggaatcgc      300
tgacgattcc caggtttctc cggcaagcat agcgcatggc gtctccatgc gagaatgtcg      360
cgcttgccgg ataaaagggg agccgctatc ggaatggacg caagccacgg ccgcagcagg      420
tgcggtcgag ggcttccagc cagttccagg gcagatgtgc cggcagaccc tcccgctttg      480
ggggaggcgc aagcccgggtc cattcggata gcatctcccc atgcaaagtg ccggccaggg      540
caatgcccgg agccggttcg aatagtgacg gcagagagac aatcaaatca tgagccaacc      600
atcttatggc ccgctgttcg aggccctggc ccactacaat gacaagctgc tggccatggc      660
caaggcccag acagagcgca ccgcccaggc gctgctgcag accaatctgg acgatctggg      720
ccaggtgctg gagcagggca gccagcaacc ctgcagctg atccaggccc agatgaactg      780
gtggcaggat cagctcaagc tgatgcagca caccctgctc aaaagcgcag gccagccgag      840
cgagccggtg atcaccccgg agcgcagcga tcgccgcttc aaggccgagg cctggagcga      900
```

```
acaacccatc tatgactacc tcaagcagtc ctacctgctc accgccaggc acctgctggc    960
ctcggtggat gccctggagg gcgtccccca gaagagccgg gagcggctgc gtttcttcac   1020
ccgccagtac gtctctgcca tggcccccag caacttcctg ccaccaacc ccgagctgct   1080 caagctgacc ctggagtccg gcggccagaa cctggtgcgc ggactggccc tcttggccga   1140
ggatctggag cgcagcgccg atcagctcaa catccgcctg accgacgaat ccgccttcga   1200
gctcgggcgg gatctggccc tgaccccggg ccgggtggtg cagcgcaccg agctctatga   1260
gctcattcag tacagcccga ctaccgagac ggtgggcaag acacctgtgc tgatagtgcc   1320
gcccttcatc aacaagtact acatcatgga catgcgcccc cagaactccc tggtcgcctg   1380
gctggtcgcc cagggccaga cggtattcat gatctcctgg cgcaacccgg gcgtggccca   1440
ggcccaaatc gatctcgacg actacgtggt ggatggcgtc atcgccgccc tggacggcgt   1500
ggaggcggcc accggcgagc gggaggtgca cggcatcggc tactgcatcg gcggcaccgc   1560
cctgtcgctc gccatgggct ggctggcggc gcggcgccag aagcagcggg tgcgcaccgc   1620
caccctgttc actaccctgc tggacttctc ccagcccggg gagcttggca tcttcatcca   1680
cgagcccatc atagcggcgc tcgaggcgca aaatgaggcc aagggcatca tggacgggcg   1740
ccagctggcg gtcagcttca gcctgctgcg ggagaacagc ctctactgga actactacat   1800
cgacagctac ctcaagggtc agagcccggt ggccttcgat ctgctgcact ggaacagcga   1860
cagcaccaat gtggcgggca agacccacaa cagcctgctg cgccgtctct acctggagaa   1920
ccagctggtg aagggggagc tcaagatccg caacacccgc atcgatctcg gcaaggtgaa   1980 gaccccctgtg ctgctggtgt cggcggtgga cgatcacatc gccctctggc agggcacctg   2040
gcagggcatg aagctgtttg cgggggagca gcgcttcctc ctggcggagt ccggccacat   2100
cgccggcatc atcaacccgc cggccgccaa caagtacggc ttctggcaca acggggccga   2160
ggccgagagc ccggagagct ggctggcagg ggcgacgcac cagggcggct cctggtggcc   2220
cgagatgatg ggctttatcc agaaccgtga cgaagggtca gagcccgtcc ccgcgcgggt   2280
cccggaggaa gggctggccc ccgccccgg ccactatgtc aaggtgcggc tcaacccgt   2340 gtttgcctgc ccaacagagg aggacgccgc atgacgcttg catgagtgcc ggcgtgcgtc   2400
atgcacggcg ccggcaggcc tgcaggttcc ctcccgtttc cattgaaagg actacacaat   2460
gactgacgtt gtcatcgtat ccgccgcccg caccgcggtc ggcaagtttg gcggctcgct   2520
ggccaagatc ccggcaccgg aactgggtgc cgtggtcatc aaggccgcgc tggagcgcgc   2580
cggcgtcaag ccggagcagg tgagcgaagt catcatgggc caggtgctga ccgccggttc   2640
gggccagaac cccgcacgcc aggccgcgat caaggccggc ctgccggcga tggtgccggc   2700
catgaccatc aacaaggtgt gcggctcggg cctgaaggcc gtgatgctgg ccgccaacgc   2760
gatcatggcg ggcgacgccg agatcgtggt ggccggcggc caggaaaaca tgagcgccgc   2820
cccgcacgtg ctgccgggct cgcgcgatgg tttccgcatg ggcgatgcca agctggtcga   2880
caccatg                                                             2887
```

<210> SEQ ID NO 3
<211> LENGTH: 742
<212> TYPE: DNA
<213> ORGANISM: Artificial Sequence
<220> FEATURE:
<223> OTHER INFORMATION: acetoacetyl CoA reductase

<400> SEQUENCE: 3

| | |
|---|---|
| atgaccagcc gcgtggccct ggtgaccggc ggcaccggcg gcatcggcac cgccatcgtg | 60 |
| aagcgcctgg cggccatggg ccacaaggtg gcgaccaact accgcgacga ggccaaggcc | 120 |
| aaggcctggg ccgacaagct gaagtcggag ggcgtggacg tgctgctggt gaagggcgac | 180 |
| gtgtcggaca ccgccagcag cgaggccatg atcaaggaga tcgagagcaa gctgggcccg | 240 |
| atcgacatcc tgatcaacaa cgcgggcatc acccgcgaca ccaccttcca caagatgtcg | 300 |
| gccatgcagt ggcaggaagt gatcaacacc aacctgaaca cgtgttcaa cgtgacccgc | 360 |
| ccggtgatcg agggcatgcg caaccgcaag tggggccgca tcatccagat ctcgagcatc | 420 |
| aacggccaga agggccagta cggccaggcc aactacgcgg ccgccaaggc gggcatgcac | 480 |
| ggcttcacca tctcgctggc gcaggagaac gccaagttcg gcatcaccgt gaacaccgtg | 540 |
| agcccgggct acgtggccac cgagatggtg atggccgtgc cggaggacgt gcgcaacaag | 600 |
| atcgccgccc agatcccggt gggccgcctg ggcgagccgg aggagatcgc gtacgccatc | 660 |
| gagttcttcg tgaaggacga ggccaagtgg atcaccggcg ccaacctggc catcaacggt | 720 |
| ggccagtaca tgggctggta ag | 742 |

<210> SEQ ID NO 4
<211> LENGTH: 729
<212> TYPE: DNA
<213> ORGANISM: Artificial Sequence
<220> FEATURE:
<223> OTHER INFORMATION: acetoacetyl CoA reductase

<400> SEQUENCE: 4

| | |
|---|---|
| atggccaagc gcaacgccat cgtgaccggc ggcacccgcg gcatcggcca cgccatcgcg | 60 |
| atcgccctga aggaagccgg ctgcaccgtg gcggccacct accacggcaa cgacgaggcc | 120 |
| gcgaaggcct tccacgagga aaccggcgtg gcggtgttca gtgggacgt gggcgactac | 180 |
| gacgcctgca aggcgggcgt ggccgagatc gagaaggccc acggcccgac cgacatcctg | 240 |
| gtgaacaacg ccggcgtgac ccgcgacggc ttcttccaca gatgaccccc ggcccagtgg | 300 |
| cgcgaggtga tccgcgcgga cctggactcg gtgttcaaca tgacccacca ggtgttcccg | 360 |
| ggcatgcgcg agcgcggctt cggccgcatc atcaacatct cgagcatcaa cggccagaag | 420 |
| ggccagatgg gccagaccaa ctacagcgcc gcgaaggcgg gcatgatcgg cttcacccgc | 480 |
| gccctggccc aggaaggcgc gttcaagggc gtgaccgtga acgccgtggc cccgggctac | 540 |
| atcgccaccg acatggtggc gaagctggac gaaaccgtgc tgcagaagat cgtggcccag | 600 |
| atcccggtgg gccgctgggg cgaggcgag gagatcgcgc gctgcgtggc cttcctggcc | 660 |
| gacgacgcgg ccggcttcat caccggcagc gtgctgaccg tgaacggtgg ccagtacatc | 720 |
| gccgcgtaa | 729 |

<210> SEQ ID NO 5
<211> LENGTH: 745
<212> TYPE: DNA
<213> ORGANISM: Artificial Sequence
<220> FEATURE:
<223> OTHER INFORMATION: acetoacetyl CoA reductase

<400> SEQUENCE: 5

| | |
|---|---|
| atgacccagc acatcgccgt ggtgaccggc gcctcgggcg gcctgggcga aaccatgtgc | 60 |
| aaggcgatgg tggaccaggg ccacaaggtg gcgggcagct acctgccggg caccgacgcc | 120 |
| gaggcgaaga gctggcagca gtcgatgcag gcggccggct acgaggtggc catctacccg | 180 |
| ctggacgtga ccaactacga caactgctgc tcgttcatcg ccaccgtgga gaaggacctg | 240 |

| ggcccgatca gcatcctggt gaacaacgcc ggcatcaccc gcgacgcccc gctgaagcgc | 300 |
| atgcagccgc agcagtggca ggacgtgctg cgcaccaacc tggactcgat gtacaacatg | 360 |
| tgccagccgg tgttcgacgc catgtgcaac cgcggcttcg ccgcatcgt gaacatctcg | 420 |
| tcgctgaacg gcgagcaggg ccagttcggc caggccaact acagcgcggc caaggccggc | 480 |
| atctacggct tcaccaaggc catcgccaag gaaggcgccc gcaagggcgt gaccgtgaac | 540 |
| gccgtgagcc cgggcttcat cgacaccccg atggtgcgcc aggtgccgga aacgtgctg | 600 |
| gagagcatca tctcgggcat cccggtgggc cgcctgggcc agccggagga tcgcccgc | 660 |
| gccgtggcct tcctgaccgc cgaggacgcg ggctacatca ccggctcgaa catcagcgtg | 720 |
| aacggcggcg agtacatgag ctaag | 745 |

<210> SEQ ID NO 6
<211> LENGTH: 724
<212> TYPE: DNA
<213> ORGANISM: Artificial Sequence
<220> FEATURE:
<223> OTHER INFORMATION: acetoacetyl CoA reductase

<400> SEQUENCE: 6

| atgaagaacg tggccatcgt gaccggcggc acccgcggca tcggcctgga gatcaccaag | 60 |
| gccctgatcg cggagggcta caaggtggcc gcgatctacc acggcaacga ggaagccgcc | 120 |
| aaggcctgcg aggccgaaac cggcgccaag gcgtacaaga tcgacgtggc cagctaccag | 180 |
| gcctgccacg acggctgcgc caagatcgag caggagatgg gcccgatcag cctgctggtg | 240 |
| aacaacgcgg gcatcaccaa ggacggcgtg ctgcacaaga tggccgagga ccagtggcac | 300 |
| gcggtgatcg aaaccaacct gacctcgtgc ttcaacatgt gcgcgcgcgg tgatcaccgg | 360 |
| catgcgcgag cgcgtgtacg gccgcatcgt gaacatctcg agcatcaacg gccagaaggg | 420 |
| ccagttcggc cagaccaact acagcgcggc caaggcgggc atgctgggct tcaccaaggc | 480 |
| cctggccctg gagtcggcgg ccaagggcat caccgtgaac gcgatctgcc cgggctacat | 540 |
| cgaaaccgag atgaccgccg cgatgaagca ggacgtgctg gactcgatcg tgcgccagat | 600 |
| cccggcggcc cgcatgggca gccgcaggga tcgccgac ctggtggtgt tcctggccag | 660 |
| cgagaaggcg ggcttcatca acggcgccac catgaccgcc aacggtggcc agtacatgat | 720 |
| ctaa | 724 |

<210> SEQ ID NO 7
<211> LENGTH: 748
<212> TYPE: DNA
<213> ORGANISM: Artificial Sequence
<220> FEATURE:
<223> OTHER INFORMATION: acetoacetyl CoA reductase

<400> SEQUENCE: 7

| atgaagaaca gcaccggccg cgtggccctg atcaccggca gcaccggcgg catcggcacc | 60 |
| gccctgtgca agaagctgtg cgaggaaggc ttccgcgtgg tgggcaactt ccgctgctgg | 120 |
| gagaaggccc aggcgatgca gaacacctg caggacgtgg gctgcgaggt ggacatgcgc | 180 |
| cagggcgacg tggcggactt cgacagcgtg ggccgcatgg tgcgcgccgt ggagtcggag | 240 |
| atcggcccga tcgacgtgct gatcaacaac gcgggcatcg cccgcgacgt gcgcttcacc | 300 |
| aagatggaga aggccgactg gacgacgtg atgaacacca acctgaacgg cgtgttcaac | 360 |
| tgcacccgcc acgtgatcga cggcatgatg gcccgtcgct acggccgcat catcaacatc | 420 |

| tcgagcatca acggccagaa gggccagttc ggccagacca actacagcgc ggccaaggcg | 480 |
| ggcatccacg gcttcaccaa gagcctggcc ctggaggtgg cgaagtacgg catcaccgtg | 540 |
| aacaccatct cgccgggcta catcgaaacc gagatggtga tggccgtgcc gcagaacatc | 600 |
| cgcgagcaga tcgtggccca gatcccggtg gccgcatgg gctacatcga ggaagtggcc | 660 |
| gaggcggtga gctacctggt gtcggacaag agcggcttca tcaccggctc gaacctgagc | 720 |
| atcaacggtg gccagcacat gtactaag | 748 |

```
<210> SEQ ID NO 8
<211> LENGTH: 751
<212> TYPE: DNA
<213> ORGANISM: Artificial Sequence
<220> FEATURE:
<223> OTHER INFORMATION: acetoacetyl CoA reductase

<400> SEQUENCE: 8
```

| atgtgcggcg acctgaagaa caaggtggcc ctggtgaccg gcggcaccgg cggcatcggc |  60 |
| accgcgatct gcgcccgcct gtcggacctg ggctgccgcg tggccaccac ctaccgcaac | 120 |
| cgcgagaagg ccgaggcctg caggcccag atgaagcaga cggccacca ggtgaccatc | 180 |
| tacgcctgcg acgtgggcga ctacgaggcc tgcgtgcagc tggccgaaac catcgagaag | 240 |
| gacctgggcc cggtggacat cctggtgaac aacgcgggca tcacccgcga caccaccctg | 300 |
| aagaagatga ccccgggcca ctggcgcgag gtgatctgcg cggacctgga ctcggtgttc | 360 |
| aacatgaccc agccgctgct gccgcgcatg gcggagcgcg gctggggccg cgtgatcaac | 420 |
| atctcgagca tcaacggcca gaagggccag ttcggccagg ccaactacag cgcggccaag | 480 |
| gcgggcatgc acggcttcac catggcggcc gcccaggaag tggcccgcaa gggcgtgacc | 540 |
| gtgaacacca tcagcccggg ctacatcgcg accgagatgg tgatggccgt gccggaggaa | 600 |
| gtgcgcgaca agatcatcgc ccagatcccg gtgggccgcc tgggccgtcc ggaggaagtg | 660 |
| gcccacgtgg tggcgttcct ggcctcggag cacgccggct tcatcaccgg cgccaacttc | 720 |
| gccgccaacg gtggccagca catgcactaa g | 751 |

```
<210> SEQ ID NO 9
<211> LENGTH: 742
<212> TYPE: DNA
<213> ORGANISM: Artificial Sequence
<220> FEATURE:
<223> OTHER INFORMATION: acetoacetyl CoA reductase

<400> SEQUENCE: 9
```

| atgtcgcagc gcaccgccct ggtgaccggc ggcaccggcg gcatcggcac cgccatcgtg |  60 |
| cgctacctga gccgccaggg ccaccgcgtg gcgaccaact accgcgacgc ggcccgcgcg | 120 |
| gaggagtggc gcaagcgcat ggcggccgag ggcatcgagg tgtgcctggt gccgggcgac | 180 |
| gtggcggacc cggccagcgc cgaggcgatg gtgcgcgccg tggaggccaa gtgcggcccg | 240 |
| gtggagatcc tggtgaacaa cgccggcatc acccgcgaca ccaccttcca caagatgacc | 300 |
| taccagcagt ggaccgacgt ggtgaacacc aacctgaacg cgtgcttcaa cgtgacccgc | 360 |
| ccggtgatcg agggcatgcg cgcccgcaag tgggccgca tcgtgcagat ctcgagcatc | 420 |
| aacggccaga agggccagta cggccaggcc aactacgcgg ccgccaaggc gggcatgcac | 480 |
| ggcttcacca tcagcctggc ccaggagaac gcccgcttcg gcatcaccgt gaacaccgtg | 540 |
| agcccgggct acgtggccac cgacatggtg atggccgtgc cggaggaagt gcgcgagaag | 600 |
| atcgtggccc agatcccggt gggccgcctg ggcaagccgg aggagatcgc ccacgcggtg | 660 |

```
gccttcttca ccaccgacga ggccagctgg atcaccggcg ccaacctggc catcaacggt    720
ggccactaca tgggctggta ag                                              742

<210> SEQ ID NO 10
<211> LENGTH: 724
<212> TYPE: DNA
<213> ORGANISM: Artificial Sequence
<220> FEATURE:
<223> OTHER INFORMATION: acetoacetyl CoA reductase

<400> SEQUENCE: 10
atgagccgcg tggtggtggt gaccggcggc acccgcggca tcggcgagga gatctgcgtg     60
gagcacaagg cggccggcta caccgtggcc gcgatctacg gtggcaacga cgaggcggcc    120
aaggccttca ccgagcgcac cggcatcaac gcctacaagt cgacgtgag cgactacgac     180 gcgtgccagg aagccgtgca ggtgatcgag aaggagctgg gcccggtgga catcctggtg    240
aacaacgccg gcatcacccg cgacggcgcc atgcacaaga tggacttcga cgctggaac    300 gcggtgatcc agaccaacct gtcgagctgc ttcaacatgt cgaaggcggt gatcgacggc    360
atgcgcgagc gcgagttcgg ccgcatcgtg aacatcggct cggtgaacgg ccgcgccggc    420
cagtacggcc aggtgaacta cgcggccgcc aagagcggca tccacggctt caccaaggcc    480
ctggccctgg agggcgccag caagggcatc accgtgaacg ccatcgcccc gggctacgtg    540
ctgaccgaca tggtgcgcgc cgtgccgcag aaggtgctgg acaagatcat cgccaccatc    600
ccggtgggcc gcctgggcga cccgggcgac atcgcgcgcg ccgtgatgtt cctgaccagc    660
gacggctcgg gcttcgtgac cggcagcacc ctggacgtga acggtggcca gcacatgtac    720
taag                                                                 724

<210> SEQ ID NO 11
<211> LENGTH: 745
<212> TYPE: DNA
<213> ORGANISM: Artificial Sequence
<220> FEATURE:
<223> OTHER INFORMATION: acetoacetyl CoA reductase

<400> SEQUENCE: 11
atgcaggacc gcatcgcctt cgtgaccggc ggcaccggcg gcatcggcag cgcgatctgc     60
aagatgctgt ggcggaggg ctgccgcgtg ccagcagct acatcccggt ggagaaggac     120
ctggccctga gtggcaggc cgagaacaag gcggagggca tcgacgtgtt cctgaccgag    180
ggcgacgtga ccgacgcggc cgactgcgag cgcatggccc aggagatcga ggacgccctg    240
ggcccgatcg acgtgctggt gaactgcgcg gcatcacccc gcgacggcac cttcaagaag    300
atggagcgcg agcagtggta cgacgtgatc gacaccaacc tgaacagcgt gtacaacgtg    360
acccgcccgg tgatcaacgg catgctggag cgcaagttcg ccgcgtgat caacatctcg    420 tcgctgaacg gccgcaaggg ccagttcggc caggccaact acagcgcggc caaggccggc    480
atgcacggct tcaccatggc cctggcccag gaaaccgcca gcaagggcat caccgtgaac    540
accatctcgc cgggctacat cggcaccagc atggtgatgg ccatcccgga ggacatccgc    600
aaccagatca tcgcgcagat cccggtgggc cgcctgggcc agccggacga gatcgccagc    660
ctggtggcct acctggcctc ggacaagggc gccttcatca ccggcgcgaa catcgacatc    720
aacggtggcc agcacatgca ctaag                                          745

<210> SEQ ID NO 12
```

```
<211> LENGTH: 745
<212> TYPE: DNA
<213> ORGANISM: Artificial Sequence
<220> FEATURE:
<223> OTHER INFORMATION: acetoacetyl CoA reductase

<400> SEQUENCE: 12
atgaagaagc acaccgtgct ggtgaccggc ggcaccggcg gcatcggcaa ggccatctgc      60
atggcgctgt cggacgaggg cttctcggtg gtggccagct gcagcggcaa ctcgtgcaag     120
aagatggaca tctggcagga agagatgaag atgcagggct acagcatccc gctggtgcgc     180
ggcgacgtgg cggacttcga cagctgcacc aagatggtgc aggacgcgga gcagctgatc     240
ggctcgatcg acatcctggt gaacgtggcc ggcatcaccc gcgacggcag cttccgcaag     300
atgagcacca cccagtggca gaacgtgatc cgcaccaacc tggacagcgt gtacaacgtg     360
acccagcagg tgatcaacgg catgatcgag cgtcgcttcg gccgcatcat caacatctcg     420
agcgtgaacg gccagaaggg ccagttcggc cagaccaact acagcgcggc caaggcgggc     480
atgcacggct tcaccatggc cctggcccag gaagtggccc acaagggcat caccgtgaac     540
accgtgagcc cgggctacat cgccaccgag atggtgatgg cggtggacga ggacatccgc     600
aaggagatcg tgaagcagat cccggtgggc cgcttcggcg agccgaggaa gatcgcccgc     660
gtggtgtcgt tcctggccga cgagcagagc ggcttcatca ccggcgccga catgagcatc     720
aacggtggca tgtacatgca ctaag                                          745

<210> SEQ ID NO 13
<211> LENGTH: 748
<212> TYPE: DNA
<213> ORGANISM: Artificial Sequence
<220> FEATURE:
<223> OTHER INFORMATION: acetoacetyl CoA reductase

<400> SEQUENCE: 13
atggacaagg tgcaggtgtg cctggtgacc ggcggcgccg gcggcatcgg ccgcgagatc      60
tgccgtcgca tggcggccga cggctacacc gtggtggccg gctgcaccag cctggacggc     120
gccaacgcca aggccttcgc ggccgagatc gagcaggacc gcctgaacat ccgcctgcgc     180
gccttcgacg tgtcggactt cgacgcgtgc cagcgcacca tcatggacat cgaggagtcg     240
gtgggcagca tcgccgtgct ggtgaacaac gccggcatca cccgcgacgg caccctgcgc     300
aagatgaacc gcgcccagtg ggacgaggtg ctgagcgtga acctggacag cgtgttcaac     360
ctgtcgcgcg cggtgatcaa cccgatgctg gagcgccagt acggccgcat catcaacatc     420
tcgagcatca acgccagaa gggccagttc ggccagtgca actacgcggc cgccaaggcc     480
gccatgtacg gcttctcgaa gtcgctggcc caggaaaccg ccgccaaggg catcaccgtg     540
aactgcatca gcccgggcta catcgaaacc gacatgatcc tggccatcga cgaaaccatc     600
cgcgactcga tccgcaagca gatcccggtg cagcgcttcg ccagccgag cgaggtggcc     660 cgcagcgtgg cgttcctggc cgcccgag gccggcttca tcaccggcag caacctggcg     720
atgaacggtg gccagtacat ggactaag                                       748

<210> SEQ ID NO 14
<211> LENGTH: 742
<212> TYPE: DNA
<213> ORGANISM: Artificial Sequence
<220> FEATURE:
<223> OTHER INFORMATION: acetoacetyl CoA reductase

<400> SEQUENCE: 14
```

```
atgaccaagc gcatcgccct ggtgaccggc ggcatgggcg gcatcggcag cgccatctgc    60
aaggccctgg ccgaggcggg ccacatcgtg gtgacgacct acagcaagcc gggccgcgag   120
caggcctggc acgcggacat gaagggcctg gcttcaacg acatccactc gtaccagtgc    180
gacgtgaccg acttcgcggc ctgccaggac atcgcggccc catcgccaa ggacatcggc    240 ccgatcagca tcctggtgaa caacgcgggc atcacccgcg acgcctcgtt caagaagcag   300
agcaaggacg actgggacgc ggtgatccgc accaacctgg actcggtgtt caacatgacc   360
aagccggtgc tggactcgat gctggaggcg ggcttcggcc gcatcgtgaa catctcgagc   420
atcaacggcc agaagggcca gttcggccag accaactaca gcgcggccaa ggccggcatg   480
cacggcttca ccatggcgct ggcccaggaa gtggccaaga agggcgtgac cgtgaacacc   540
atctcgccgg gctacatcgc gaccgagatg gtgatggcgg tgccggagga cgtgcgcagc   600
aagatcgtgg cccagatccc ggtgggccgc ctgggcaagc cggaggagat cgcggccctg   660
gtgggcttcc tgtgcagcga gaacgcgggc ttcatcaccg gcagcaacat cgccatgaac   720
ggtggccagc acatgatgta ag                                            742

<210> SEQ ID NO 15
<211> LENGTH: 739
<212> TYPE: DNA
<213> ORGANISM: Artificial Sequence
<220> FEATURE:
<223> OTHER INFORMATION: acetacetyl CoA reductase

<400> SEQUENCE: 15
atgaccaacc gcgtggccct ggtgaccggc ggcatgggcg gcatcggcaa cgccatctgc    60
aaggccctgg gcaaggcggg ccacaccgtg gtgaccacct actcgaagcc gggccgcgag   120
gacgcctggg tggccgagat gaagaccctg gcatctcgg cccacgccta cccgtgcgac    180
gtgaccgacg cggcccagtg cgcggccctg gtggcgcagg tgtcgtcgga gatcggcccg   240
gtggccgtgc tggtgaacaa cgcgggcatc acccgcgacg gcaccctgcg caagatgagc   300
gcggaggact ggtcggcggt gctgccacc aacctggaca gcgtgttctt catggcacgc   360
ccggtgatcg acggcatgct ggacgcgggc tggggccgca tcatcaacat ctcgagcatc   420
aacggccaga agggccagtt cggccagacc aactacagcg cggccaaggc cggcatgcac   480
ggcttcacca tggccctggc ccaggaagtg cccgcaagg gcgtgaccgt gaacaccatc   540
agcccgggct acatcgcgac cgagatggtg atggccgtgc cggaggacgt gcgcaacaag   600
atcatcggcc agatcccggt gggccgcctg gcaccccgg aggagatcgc cggcctggtg   660
acctacctgg ccagcgacat cgccggcttc atcaccggcg ccaacctgag catcaacggt   720
ggccagcaca ccatgtaag                                                739

<210> SEQ ID NO 16
<211> LENGTH: 739
<212> TYPE: DNA
<213> ORGANISM: Artificial Sequence
<220> FEATURE:
<223> OTHER INFORMATION: acetoacetyl CoA reductase

<400> SEQUENCE: 16
atgatcaaga ccgccctgat caccggcggc atgggcggca tcggcgagat cgtggccaag    60
aagctgcacg acgcgggcta ccgcgtgatc gtgaccccact cgagccgcaa cacccgcaag   120
aagatgtggc aggcggactg cctgaaggcc ggctacgact tcatctgcgt ggaggtggac   180
```

-continued

```
gtggaggaca tcgagtcgac ccgcaagatg gccaaccaca tcgcggacct gggctaccac      240
gtggacatca tcatcaacaa cgccggcatc accaaggaca tcagcttcaa gaagatgacc      300
tacgacgact ggaacatcgt gatccgcacc aacctggact cgctgtacaa cgtgaccagc      360
cagttcatca acaagatgat cgagaagaac tggggccgcg tgatcaacat ctcgagcatc      420
aacggctcga agggccagtt cggccagacc aactacgcgg ccagcaaggc cggcgtgatc      480
ggcttcacca agtcgctggc cctggaggtg gccgacaagg gcatcaccgt gaactgcatc      540
tcgccgggct accaggaaac cgccatggtg aacgcggtgg acccgctgat cctgcagcag      600
atcatcagca ccatcccgat gaagcgcctg ggccagccgc gcgagatcgc cgacctggtg      660
ctgtacctgt gctcggacac cagcgagttc atgaccggcg cgaacctgca catcaacggt      720
ggccagtaca tgggctaag                                                  739

<210> SEQ ID NO 17
<211> LENGTH: 730
<212> TYPE: DNA
<213> ORGANISM: Artificial Sequence
<220> FEATURE:
<223> OTHER INFORMATION: acetoacetyl CoA reductase

<400> SEQUENCE: 17
atgagcaagg tggccctggt gaccggcggc accggcggca tcggcagcgc cgtgtgcaag       60
cgcctggccg cggccggctt caaggtgatc agcacctact cgagccgga ggagcaggcc      120 aaggcctggg ccgagaagca ggacttcgcg gtgggcctgt accactgcaa cgtgtcggac      180
tacgacagct gcgtgaagct gaagcaggcc atcgaggcgg acggcctgaa cgtggacgtg      240
atcgtgaaca acgccggcat cacccgcgac gcgaagttct cgaagatgac ctacgacatg      300
tggcgcgccg tgctgtcgac caacctggac agcctgttca acatctcgca ccagttcgtg      360
gacggcatga ccgagcgcgg ctggggccgc atcatcaaca tctcgtcggt gaacggccag      420
aagggccagg cggccagac caactactcg gccgccaagg ccggcgtgca cggcttcacc      480
atggccctgg cccaggaagt ggtgcgcaag ggcgtgaccg tgaacaccat ctcgccgggc      540
tacatcggca ccgagatggt gatggccatc cgcgaggacg tgcgcgagaa gatcgtggcc      600
cagatcccga tgcagcgcct gggcaagccg gaggagatcg ccgcggtggc caacttcctg      660
gcctcggacg acgccgcctt catcaccggc gcggacttca cgccaacgg tggccagtac      720 atgcactaag                                                             730

<210> SEQ ID NO 18
<211> LENGTH: 775
<212> TYPE: DNA
<213> ORGANISM: Artificial Sequence
<220> FEATURE:
<223> OTHER INFORMATION: acetoacetyl CoA reductase

<400> SEQUENCE: 18
atgaccaccg acaacccgac cgcgaacaag aagatcgccc tggtgaccgg cgccctgggc       60
ggcatcggca ccgccatctg ccacgccctg atccaggccg gctaccacat catcgccacc      120
tacacccaca aggccgacag caccgtgaac cgcggcgagg cctggctgaa ggaagagggc      180
atgaacggct cggacttcac cttcgtggaa ccaacctga ccgaccacga ggcggccacc      240
aaggccatcg tggacgcgat cgagaaggcc ggccacatcg acgtgctggt gaacaacgcg      300
ggcatcaccc gcgacaccac cttcaagaag atgacctacg agcagtggtc ggaggtgatc      360
gacaccaacc tgaagagcct gttcaccgtg acccagccgg tgttcaacaa gatgctggag      420
```

```
cagaagtcgg gccgcatcgt gagcatctcg agcatcaacg gcctgaaggg ccagttcggc    480
cagaccaact actcggcgac caaggccggc atcatcggct tcagcaaggc cctggcccag    540
gaaggcgcca agagcggcgt gaccgtgaac gtggtggccc cgggctacac cggcaccaag    600
atggtgatgg ccgtgccgga aaggtgatg gagagcatca aggcgggcat cccgatgggc    660
cgcatcgccc agccggagga gatcgcggcc gccgtgatgt acctggtgtc ggacggcgcc    720
gcctacatca ccggcgaaac catcaacgtg aacggtggcc agtacatgca ctaag         775
```

<210> SEQ ID NO 19
<211> LENGTH: 742
<212> TYPE: DNA
<213> ORGANISM: Artificial Sequence
<220> FEATURE:
<223> OTHER INFORMATION: acetacetyl CoA reductase

<400> SEQUENCE: 19

```
atgcagaagc tggccctgat caccggcagc aagggcggca tcggctcggc catcaccgag     60
aagctggtgc aggacggctt ccgcatcatc gcgacctact tcaccggcaa ctacgagtgc    120
gccaaggagt ggttcgacga aagggcttc agcgaggacc aggtgaccct gttcgagctg     180
gacgtgaccg acgcggacag ctgccgcgag cgcctgacca gctgctgga gaacgagggc    240 accgtggacg tgctggtgaa caacgcgggc atcacccgcg actgcacctt caagcgcatg    300
accgccgagc agtggaacga cgtgatcaac accaacctga cagcgtgtt caacgtgacc    360 cagccgctgt tcgcggccat gtgcgagaag ggcggcggcc gcatcatcaa catctcgagc    420
gtgaacggcc tgaagggcca gttcggccag accaactact cggccgcgaa ggcgggcatg    480
atcggcttca gcaaggccct ggccttcgag ggcgcccgca gcggcgtgac cgtgaacgtg    540
gtggccccgg gctacaccgg cacccccgatg gtgcaggcca tccgccagga cgtgctggac    600
agcatcatcg aaaccgtgcc gatgaagcgc ctggccaccc cggaggagat cgccagcgcc    660
gtggcctacc tggcctcgga cgccggcgcc tacatcaccg gcgaaaccct gagcgtgaac    720
ggcggcctgt acatgcagta ag                                              742
```

<210> SEQ ID NO 20
<211> LENGTH: 748
<212> TYPE: DNA
<213> ORGANISM: Artificial Sequence
<220> FEATURE:
<223> OTHER INFORMATION: acetoacetyl CoA reductase

<400> SEQUENCE: 20

```
atgacccaga agaagatcgc cctggtgacc ggcgcggcag gcggcatcgg caccgagatc     60
tgccgccagc tggccaacaa cggcttccgc gtggtggcca ccaccgccc gggcaaggcc    120 gagcaggccc aggcgtggct gcaggagcag aacctggccg accaggacat caagctgctg    180
gccctggacg tggccgacca cgagggcgtg tcgcaggccc tgggcgagct gctgaaggcc    240
gagggccgca tcgacgtgct ggtgaacaac gcgggcatca cccgcgacag cgtgttcaag    300
aagatgaccc tggagcagtg gcgcgacgtg atgtcgacca acctggacag cctgttctcg    360
gtgagccagc cggtgttcaa cgccatgtgc gagcagggcg cggccgcat catcaacatc    420 tcgagcgtga acggcctgaa gggccagttc ggccaggtga actactcggc cgcgaaggcg    480
ggcatgatcg gcttcaccaa ggccctggcc gccgagggcg cccgcttcgg cgtgtgcgtg    540
aacgcggtgg ccccgggcta caccgccacc ccgatggtga ccgccatccg cgaggacgtg    600
```

```
ctggactcga tcaaggccac catcccgctg aagcgcctgg ccaccaccga ggaagtggcg      660
ggcgccgtgc tgtacctggc gggcgagcac ggtggctacg tgaccggcga acccctgtcg      720
gtgaacggcg gcctgtacat gcagtaag                                        748
```

<210> SEQ ID NO 21
<211> LENGTH: 748
<212> TYPE: DNA
<213> ORGANISM: Artificial Sequence
<220> FEATURE:
<223> OTHER INFORMATION: acetoacetyl CoA reductase

<400> SEQUENCE: 21

```
atgaccaaga aggtggccct ggtgaccggc ggcaccggcg gcatcggcac ccagatctgc       60
cgcaccctga gcaccgccgg ctacatcgtg gtggccaact ggctgaaggg catcgacgac      120
ggcccggcct gggaggcgaa gcagaaggcg gacggctacg acaacatcct gatcgccgag      180
ggcgacgtga gcgactacga ccaggccgtg gcgatggtga aggaagccgt ggagaaggcg      240
ggcgccccga tcgacatcct ggtgaacaac gccggcatca cccgcgacaa gatgttccgc      300
aagatggaga gtcgcagtg ggacgcggtg atcaacagca acctgtcgag catcttcaac      360
gtgaccaagc aggtgctgga cggcatggtg gagcgcggct ggggccgcat cgtgaacatc      420
tcgtcggtga acggccagaa gggccaggcg ggccaggcca actacagcgc ggccaaggcc      480
ggcatgcacg gcttcaccat ggccatcgcg caggaagtgg cctcgaaggg cgtgaccgtg      540
aacaccatca gcccgggcta catcggcacc gccatggtga tgagcatcaa ggaagagatc      600
cgcaaccaga tcgtggccca gatcccggtg gccgcctgg caagccgga ggagatcgcc      660 tggaccgtgc agttcctggc cgacgagaag tcggcgttca tcaccggcgc caacatctcg      720
gtgaacggcg gcctgcacat gggctaag                                        748
```

<210> SEQ ID NO 22
<211> LENGTH: 751
<212> TYPE: DNA
<213> ORGANISM: Artificial Sequence
<220> FEATURE:
<223> OTHER INFORMATION: acetoacetyl CoA reductase

<400> SEQUENCE: 22

```
atgacctcgg aaaccaagcg caccgccctg gtgaccggcg gcatcggcgg cctgggcacc       60
gccatcgcgc gctcgctggc cgaccgcggc caccaggtgc tggtggcgta ctacgtgagc      120
gacaacccga ccgagtggct ggccaagcag aaggaagacg gctacgactt caaggcctac      180
gcggtggacg tggcggactt cgagtcgtgc cagcagatgg tggagaagat ccacgtggac      240
ggcttcaaga tcgacatcct ggtgaacaac gccggcatca ccaaggaccg ctcgttccgc      300
aagatgagct acgaggactg ggaggcggtg ctgcgcacca acctggacag cgtgttcaac      360
gtgaccaagc aggtgatcga cgacatgctg gagtcgaagt ggggccgcat cgtgaccatc      420
tcgagcgtga acggcagcaa gggccagttc ggccaggcca actactcgag cgcgaagtcg      480
ggcatgtacg gcttcagcaa gacctggc ctggagttcg cggccaaggg catcaccgtg       540
aacaccgtga gcccgggcta catcatgacc gagatggtgg cgcagatgcc gcaggagatc      600
gtgaacgagc agatcatccc gcagatcccg atgcgtcgcc tgggcaagcc ggaggagatc      660
ggcgagctgg tggcctacat ctgcagcgag tcggccggct tcatgaccgg cgccaacatc      720
gccatcaacg gcggcctgca catgtactaa g                                    751
```

<210> SEQ ID NO 23
<211> LENGTH: 742
<212> TYPE: DNA
<213> ORGANISM: Artificial Sequence
<220> FEATURE:
<223> OTHER INFORMATION: acetoacetyl CoA reductase

<400> SEQUENCE: 23

```
atgaccgagc gcatcgcctt cgtgaccggc ggcatgggcg gcatcggcac cgccatctgc      60
aagcgcctgg cggccaacgg caacaaggtg gtggccaact gcctgccggg ctacgacaag     120
aaggacgact ggctgagctc gatgcgcgcc cagggctaca gcgtgcacgc ggccgagggc     180
aacgtggagg agttcgactc cgtgcgccgac atgttctacc gcatcggcag catcatcggc    240
ccggtggaca tcctggtgaa caacgcgggc atcacccgcg acggcgtgtt caagcgcatg     300
tcggagagcg actggtacga cgtgatcaac accaacctga cagcgtgtt caacgtgacc     360
cgccaggtgg tggagggcat gaccgaccgc ggctggggcc gcatcatcaa cgtgtcgagc     420
gtgaacgccc tgaagggcca gttcggccag accaactaca gcgcggccaa ggccggcatg     480
cacggcttca gcaaggccct ggcccaggaa gtggtgcgca agggcgtgac cgtgaacacc     540
atctcgccgg gctacgtggc caccgagatg gtgatggcga tccgcaccga ggtgcgcgac     600
cagatcgtgg ccaccatccc gatgggccgc ctggcccagc cggacgagat cgccggcctg     660
gtggcctacc tggccagcga cgacgcgggc tacatcaccg cgcgaacat cagcatcaac     720
ggcggcctgc acatggccta ag                                              742
```

<210> SEQ ID NO 24
<211> LENGTH: 748
<212> TYPE: DNA
<213> ORGANISM: Artificial Sequence
<220> FEATURE:
<223> OTHER INFORMATION: acetoacetyl CoA reductase

<400> SEQUENCE: 24

```
atgggcagca ccagccgcat cgcggtggtg accggcggca tgggcggcat cggcaccagc      60
atcagccagc gcctgcacaa ggaaggcttc aaggtggtgg tgacctgcag cccgaactcg     120
agccgcaaga acgactggct gccgatccag cagaaggcgg gctacgactt cgagtgcgtg     180
gagatggacg tgaccgactg ggagagcacc aagaacgccc tgaagcaggt gcacgaggag     240
ttcggcccgg tggcggtgct ggtgaacaac gccggcatca cccgcgacgc cagcttccgc     300
aagctgaccc cggaggactg gaacgcggtg atcggcacca acctgaccag cctgttcaac     360
acctcgaagc aggtgctgga cggcatgctg gccaacggct ggggccgcat catcaacatc     420
tcgtcgatca acggccagcg cggccagttc ggccagacca actacagcgc ggccaaggcc     480
ggcatccacg gcttcaccat ggccctggcc cgcgaggtga cggcaaggg cgtgaccgtg     540
aacaccgtgt cgccgggcta catccagacc gacatgaccg ccgcgatccg ccaggacatc     600
ctggacacca tgatcgcggc caccccggtg ggccgcctgg ccgtccgga ggagatcgcc     660
agcatcgtgg cctggctggc cagcgaggag tcggcctaca gcaccggcgc cgacttctcg     720
atcaacggtg gcatgaacat gcagtaag                                       748
```

<210> SEQ ID NO 25
<211> LENGTH: 748
<212> TYPE: DNA
<213> ORGANISM: Artificial Sequence
<220> FEATURE:
<223> OTHER INFORMATION: acetacetyl CoA reductase

<400> SEQUENCE: 25

```
atgaccgaca gcgcccgcat cgccctggtg accggcggca tgggcggcat cggcaccgcc    60
atctcgcagc gcctgcaccg cgagggcttc accgtggtgg tgggctgcag cccggccagc   120
agccgcaaga cgactggat cagccgccag caggaagccg gctaccactt ccactgcgtg    180
gactgcgaca tcaccgactg ggagagcacc cgccagggct tcgagctggt gcgcgagtcg   240
gtgggcccga tcgacgtgct ggtgaacaac gcgggcatca cccgcgacgc caccttccgc   300
aagctgaccc cggagaactg gcgcgccgtg atcgaaacca acctgaacgg cctgttcaac   360
accaccaagc aggtgatcga cagcatgctg gcccgcaact ggggccgcat catcaacatc   420
tcgtcgatca acggccagcg cggccagttc ggccagacca actactcggc ggccaaggcg   480
ggcatccacg gcttcaccat ggccctggcc cgcgaggtgt cgggcaaggg cgtgaccgtg   540
aacaccgtga gcccgggcta catccagacc gacatgaccc cggccatccg cccggacatc   600
ctggagggca tgatcgcggg catcccggtg ggccgcctgg gccagccgga ggagatcgcc   660
agcatcgtgg cctggctggc cagcaccgag tcggcctacg ccaccggcgc cgacttctcg   720
gtgaacggtg gcatgaacat gcagtaag                                      748
```

<210> SEQ ID NO 26
<211> LENGTH: 748
<212> TYPE: DNA
<213> ORGANISM: Artificial Sequence
<220> FEATURE:
<223> OTHER INFORMATION: acetoacetyl CoA reductase

<400> SEQUENCE: 26

```
atgaacaccg agaaccagca catcgccctg gtgaccggcg ccaccggcgg cctgggcacc    60
cacatctgca gcgcctgtc ggaggacggc tacatcgtgt gcgccaacta ccgcagcgag   120
gagaaggcgc aggagtggaa gaagaagatg gaggccgagg gctaccagtt ctacctgtac   180
aaggcggacg tgtgcgacta cgacgccgtg agcagatga tcaaggcgat cgagcaggac   240
cacggcgtgg tggacatcct ggtgaacaac gccggcatca ccaaggacgg catcttcaag   300
aagatgtcga aggagaactg gcaggacgtg atcgcgacca acctgaccag cgtgttcaac   360
tgctgccgcc acgtgatcaa ccagatgatc gaccagaatt acggccgcat cgtgaacatc   420
tcgtcggtga acgccagcg cgcccagttc ggccaggtga actacgcggc cgccaaggcc   480
ggcatgcacg gcatcaccaa gaccctggcg atcgaggtgg ccaacaaggg catcaccgtg   540
aacaccatct cgccgggcta cgtggcgacc gacatggtga tggccgtgcc ggaggaagtg   600
cgcaacaaga tcatcgcggg catcccggtg gccgcctgg gcggcaccgg cgagatcgcc   660
cacctggtga gcttcctggc cgcccgcgac accgccttca tcaccggcgc gaactacgcc   720
atcaacggtg gccagcacgt gtactaag                                      748
```

<210> SEQ ID NO 27
<211> LENGTH: 745
<212> TYPE: DNA
<213> ORGANISM: Artificial Sequence
<220> FEATURE:
<223> OTHER INFORMATION: acetoacetyl CoA reductase

<400> SEQUENCE: 27

```
atgaccaagc gcatcgcggt ggtgaccggc ggcatgggcg gcctgggcga ggcggtgtcg    60
atccgcctga cgacgcggg ccaccgcgtg gtggtgacct acagcccgag caacaccggc   120
gccgaccgct ggctgaccga gatgcacgcc accggccgcg agttccacgc ctacccggtg   180
```

```
gacgtggcgg accacgacag ctgccagcag tgcatcgaga agatcgcccg cgacgtgggc    240
ccggtggaca tcctggtgaa caacgcgggc atcacccgcg acatgaccct gcgcaagctg    300
gacaaggtga actgggacgc ggtgatccgc accaacctgg actcggtgtt caacatgacc    360
aagccggtgt gcgagagcat ggtggagcgc ggctgggggcc gcatcgtgaa catctcgtcg    420
gtgaacggca gcaagggctc ggtgggccag accaactacg cggccgccaa ggcgggcatg    480
cacggcttca ccaagagcct ggccctggag atcgcccgca agggcgtgac cgtgaacacc    540
gtgagcccgg gctacctggc gaccaagatg gtgaccgcca tcccgcagga catcctggac    600
tcgaagatcc tgccgcagat cccggccggc cgcctgggca gccggagga agtggccgcc    660 ctggtggcct acctgtgcag cgaggaagcc ggcttcgtga ccggcagcaa catcgccatc    720
aacggtggcc agcacatgca ctaag                                        745

<210> SEQ ID NO 28
<211> LENGTH: 742
<212> TYPE: DNA
<213> ORGANISM: Artificial Sequence
<220> FEATURE:
<223> OTHER INFORMATION: acetoacetyl CoA reductase

<400> SEQUENCE: 28
atgctgcgcg tggccctggt gaccggcggc atgggcggcc tgggcgaggc gatctgcatc     60
aagctggccg cgctgggcta caaggtggtg accacctact cgccgagcaa caccaaggcc    120
cacgagtggc tgcgcaccat gaacgacatg ggctacggct tcaaggccta cccgtgcgac    180
gtgggcgact cgactcgtg caaggcgtgc gtggagcagg tgagcaagga cgtgggcgcg    240
gtggaggtgc tggtgaacaa cgcgggcatc acccgcgaca tgaccttcaa gaagatgacc    300
aaggccgact gggacgcggt gatccacacc aacctggact cgtgcttcaa catgaccaag    360
caggtgatgg acggcatgat ggagcgcggc tggggccgcg tgatcaacat ctcgtcggtg    420
aacggccaga agggcgccct cggccagacc aactacagcg cggccaaggc cggcatgcac    480
ggcttcacca aggccctggc cctggaggtg gccaagaagg gcgtgaccgt gaacaccatc    540
agcccgggct acatcggcac caagatggtg atggcgatcc cgcaggaagt gctggagtcg    600
aagatcctgc cgcagatccc gcagtcgcgc ctgggcaagc cggaggaagt ggcgggcctg    660
gtggcctacc tgagctcgga ggaagccgcc ttcgtgaccg cgccaacat cagcatcaac    720 ggtggccagc acatgtacta ag                                          742

<210> SEQ ID NO 29
<211> LENGTH: 593
<212> TYPE: PRT
<213> ORGANISM: Artificial Sequence
<220> FEATURE:
<223> OTHER INFORMATION: PHA polymerase

<400> SEQUENCE: 29

Met Ser Gln Pro Ser Tyr Gly Pro Leu Phe Glu Ala Leu Ala His Tyr
1               5                   10                  15

Asn Asp Lys Leu Leu Ala Met Ala Lys Ala Gln Thr Glu Arg Thr Ala
            20                  25                  30

Gln Ala Leu Leu Gln Thr Asn Leu Asp Asp Leu Gly Gln Val Leu Glu
        35                  40                  45

Gln Gly Ser Gln Gln Pro Trp Gln Leu Ile Gln Ala Gln Met Asn Trp
    50                  55                  60
```

```
Trp Gln Asp Gln Leu Lys Leu Met Gln His Thr Leu Leu Lys Ser Ala
 65                  70                  75                  80

Gly Gln Pro Ser Glu Pro Val Ile Thr Pro Glu Arg Ser Asp Arg Arg
                 85                  90                  95

Phe Lys Ala Glu Ala Trp Ser Glu Gln Pro Ile Tyr Asp Tyr Leu Lys
            100                 105                 110

Gln Ser Tyr Leu Leu Thr Ala Arg His Leu Leu Ala Ser Val Asp Ala
        115                 120                 125

Leu Glu Gly Val Pro Gln Lys Ser Arg Glu Arg Leu Arg Phe Phe Thr
    130                 135                 140

Arg Gln Tyr Val Ser Ala Met Ala Pro Ser Asn Phe Leu Ala Thr Asn
145                 150                 155                 160

Pro Glu Leu Leu Lys Leu Thr Leu Glu Ser Gly Gly Gln Asn Leu Val
                165                 170                 175

Arg Gly Leu Ala Leu Leu Ala Glu Asp Leu Glu Arg Ser Ala Asp Gln
            180                 185                 190

Leu Asn Ile Arg Leu Thr Asp Glu Ser Ala Phe Glu Leu Gly Arg Asp
        195                 200                 205

Leu Ala Leu Thr Pro Gly Arg Val Val Gln Arg Thr Glu Leu Tyr Glu
    210                 215                 220

Leu Ile Gln Tyr Ser Pro Thr Thr Glu Thr Val Gly Lys Thr Pro Val
225                 230                 235                 240

Leu Ile Val Pro Pro Phe Ile Asn Lys Tyr Tyr Ile Met Asp Met Arg
                245                 250                 255

Pro Gln Asn Ser Leu Val Ala Trp Leu Val Ala Gln Gly Gln Thr Val
            260                 265                 270

Phe Met Ile Ser Trp Arg Asn Pro Gly Val Ala Gln Ala Gln Ile Asp
        275                 280                 285

Leu Asp Asp Tyr Val Val Asp Gly Val Ile Ala Ala Leu Asp Gly Val
    290                 295                 300

Glu Ala Ala Thr Gly Glu Arg Glu Val His Gly Ile Gly Tyr Cys Ile
305                 310                 315                 320

Gly Gly Thr Ala Leu Ser Leu Ala Met Gly Trp Leu Ala Ala Arg Arg
                325                 330                 335

Gln Lys Gln Arg Val Arg Thr Ala Thr Leu Phe Thr Thr Leu Leu Asp
            340                 345                 350

Phe Ser Gln Pro Gly Glu Leu Gly Ile Phe Ile His Glu Pro Ile Ile
        355                 360                 365

Ala Ala Leu Glu Ala Gln Asn Glu Ala Lys Gly Ile Met Asp Gly Arg
    370                 375                 380

Gln Leu Ala Val Ser Phe Ser Leu Leu Arg Glu Asn Ser Leu Tyr Trp
385                 390                 395                 400

Asn Tyr Tyr Ile Asp Ser Tyr Leu Lys Gly Gln Ser Pro Val Ala Phe
                405                 410                 415

Asp Leu Leu His Trp Asn Ser Asp Ser Thr Asn Val Ala Gly Lys Thr
            420                 425                 430

His Asn Ser Leu Leu Arg Arg Leu Tyr Leu Glu Asn Gln Leu Val Lys
        435                 440                 445

Gly Glu Leu Lys Ile Arg Asn Thr Arg Ile Asp Leu Gly Lys Val Lys
    450                 455                 460

Thr Pro Val Leu Leu Val Ser Ala Val Asp Asp His Ile Ala Leu Trp
465                 470                 475                 480

Gln Gly Thr Trp Gln Gly Met Lys Leu Phe Gly Gly Glu Gln Arg Phe
```

```
                485                 490                 495
Leu Leu Ala Glu Ser Gly His Ile Ala Gly Ile Ile Asn Pro Pro Ala
            500                 505                 510

Ala Asn Lys Tyr Gly Phe Trp His Asn Gly Ala Glu Ala Glu Ser Pro
            515                 520                 525

Glu Ser Trp Leu Ala Gly Ala Thr His Gln Gly Gly Ser Trp Trp Pro
            530                 535                 540

Glu Met Met Gly Phe Ile Gln Asn Arg Asp Glu Gly Ser Glu Pro Val
545                 550                 555                 560

Pro Ala Arg Val Pro Glu Glu Gly Leu Ala Pro Ala Pro Gly His Tyr
                565                 570                 575

Val Lys Val Arg Leu Asn Pro Val Phe Ala Cys Pro Thr Glu Glu Asp
                580                 585                 590

Ala

<210> SEQ ID NO 30
<211> LENGTH: 146
<212> TYPE: DNA
<213> ORGANISM: Artificial Sequence
<220> FEATURE:
<223> OTHER INFORMATION: promoter

<400> SEQUENCE: 30
atgcctccac accgctcgtc acatcctgtt gcgttcactg gaatcccacg atagagtttg      60
acctgcgagc aagctgtcac cggatgtgct ttccggtctg atgagtccgt gaggacgaaa    120
cagcctctac aaataatttt gtttaa                                         146

<210> SEQ ID NO 31
<211> LENGTH: 246
<212> TYPE: PRT
<213> ORGANISM: Artificial Sequence
<220> FEATURE:
<223> OTHER INFORMATION: wild type acetoacetyl CoA reductase

<400> SEQUENCE: 31

Met Thr Gln Arg Ile Ala Tyr Val Thr Gly Gly Met Gly Gly Ile Gly
1               5                  10                  15

Thr Ala Ile Cys Gln Arg Leu Ala Lys Asp Gly Phe Arg Val Val Ala
            20                  25                  30

Gly Cys Gly Pro Asn Ser Pro Arg Arg Glu Lys Trp Leu Glu Gln Gln
        35                  40                  45

Lys Ala Leu Gly Phe Asp Phe Ile Ala Ser Glu Gly Asn Val Ala Asp
    50                  55                  60

Trp Asp Ser Thr Lys Thr Ala Phe Asp Lys Val Lys Ser Glu Val Gly
65                  70                  75                  80

Glu Val Asp Val Leu Ile Asn Asn Ala Gly Ile Thr Arg Asp Val Val
                85                  90                  95

Phe Arg Lys Met Thr Arg Ala Asp Trp Asp Ala Val Ile Asp Thr Asn
            100                 105                 110

Leu Thr Ser Leu Phe Asn Val Thr Lys Gln Val Ile Asp Gly Met Ala
        115                 120                 125

Asp Arg Gly Trp Gly Arg Ile Val Asn Ile Ser Ser Val Asn Gly Gln
    130                 135                 140

Lys Gly Gln Phe Gly Gln Thr Asn Tyr Ser Thr Ala Lys Ala Gly Leu
145                 150                 155                 160

His Gly Phe Thr Met Ala Leu Ala Gln Glu Val Ala Thr Lys Gly Val
```

```
            165                 170                 175
Thr Val Asn Thr Val Ser Pro Gly Tyr Ile Ala Thr Asp Met Val Lys
        180                 185                 190

Ala Ile Arg Gln Asp Val Leu Asp Lys Ile Val Ala Thr Ile Pro Val
        195                 200                 205

Lys Arg Leu Gly Leu Pro Glu Glu Ile Ala Ser Ile Cys Ala Trp Leu
        210                 215                 220

Ser Ser Glu Glu Ser Gly Phe Ser Thr Gly Ala Asp Phe Ser Leu Asn
225                 230                 235                 240

Gly Gly Leu His Met Gly
            245

<210> SEQ ID NO 32
<211> LENGTH: 20
<212> TYPE: DNA
<213> ORGANISM: Artificial Sequence
<220> FEATURE:
<223> OTHER INFORMATION: pK R primer

<400> SEQUENCE: 32
gcagacttgg ccgggtacca                                          20

<210> SEQ ID NO 33
<211> LENGTH: 19
<212> TYPE: DNA
<213> ORGANISM: Artificial Sequence
<220> FEATURE:
<223> OTHER INFORMATION: pK F primer

<400> SEQUENCE: 33
caccgctcgt cacatcctg                                           19

<210> SEQ ID NO 34
<211> LENGTH: 40
<212> TYPE: DNA
<213> ORGANISM: Artificial Sequence
<220> FEATURE:
<223> OTHER INFORMATION: phaCh1 F primer

<400> SEQUENCE: 34
tggtacccgg ccaagtctgc gggcgtgccc atgatgtaga                    40

<210> SEQ ID NO 35
<211> LENGTH: 42
<212> TYPE: DNA
<213> ORGANISM: Artificial Sequence
<220> FEATURE:
<223> OTHER INFORMATION: phaCH1 R primer

<400> SEQUENCE: 35
tgagacccaa ggtctccatg atttgattgt ctctctgccg tc                 42

<210> SEQ ID NO 36
<211> LENGTH: 38
<212> TYPE: DNA
<213> ORGANISM: Artificial Sequence
<220> FEATURE:
<223> OTHER INFORMATION: phaCH2 F primer

<400> SEQUENCE: 36
ggagaccttg ggtctcagtg acgcttgcat gagtgccg                      38

<210> SEQ ID NO 37
```

```
<211> LENGTH: 39
<212> TYPE: DNA
<213> ORGANISM: Artificial Sequence
<220> FEATURE:
<223> OTHER INFORMATION: phaCH R primer

<400> SEQUENCE: 37
caggatgtga cgagcggtgc atggtgtcga ccagcttgg                    39

<210> SEQ ID NO 38
<211> LENGTH: 11
<212> TYPE: DNA
<213> ORGANISM: Artificial Sequence
<220> FEATURE:
<223> OTHER INFORMATION: primer

<400> SEQUENCE: 38
gtgaagagac c                                                  11

<210> SEQ ID NO 39
<211> LENGTH: 21
<212> TYPE: DNA
<213> ORGANISM: Artificial Sequence
<220> FEATURE:
<223> OTHER INFORMATION: FphaCH1 F primer

<400> SEQUENCE: 39
tggtctggct ggcggactga g                                       21

<210> SEQ ID NO 40
<211> LENGTH: 21
<212> TYPE: DNA
<213> ORGANISM: Artificial Sequence
<220> FEATURE:
<223> OTHER INFORMATION: phaCH2 R primer

<400> SEQUENCE: 40
ggcgaactca tcctgcgcct c                                       21

<210> SEQ ID NO 41
<211> LENGTH: 24
<212> TYPE: DNA
<213> ORGANISM: Artificial Sequence
<220> FEATURE:
<223> OTHER INFORMATION: pKCH C R primer

<400> SEQUENCE: 41
catgatttga ttgtctctct gccg                                    24

<210> SEQ ID NO 42
<211> LENGTH: 20
<212> TYPE: DNA
<213> ORGANISM: Artificial Sequence
<220> FEATURE:
<223> OTHER INFORMATION: pKCH C F primer

<400> SEQUENCE: 42
gtgacgcttg catgagtgcc                                         20

<210> SEQ ID NO 43
<211> LENGTH: 39
<212> TYPE: DNA
<213> ORGANISM: Artificial Sequence
<220> FEATURE:
<223> OTHER INFORMATION: phaB F primer

<400> SEQUENCE: 43
```
agagagacaa tcaaatcatg actcagcgca ttgcgtatg                              39

<210> SEQ ID NO 44
<211> LENGTH: 40
<212> TYPE: DNA
<213> ORGANISM: Artificial Sequence
<220> FEATURE:
<223> OTHER INFORMATION: phaB R primer

<400> SEQUENCE: 44
ggcactcatg caagcgtcac tcagcccata tgcaggccgc                             40

<210> SEQ ID NO 45
<211> LENGTH: 39
<212> TYPE: DNA
<213> ORGANISM: Artificial Sequence
<220> FEATURE:
<223> OTHER INFORMATION: iphaCH1 F primer

<400> SEQUENCE: 45
tggtacccgg ccaagtctgt gtggaactac gtggtcgac                              39

<210> SEQ ID NO 46
<211> LENGTH: 42
<212> TYPE: DNA
<213> ORGANISM: Artificial Sequence
<220> FEATURE:
<223> OTHER INFORMATION: iphaCH1 R primer

<400> SEQUENCE: 46
tgagacccaa ggtctccatt catgccttgg ctttgacgta tc                          42

<210> SEQ ID NO 47
<211> LENGTH: 40
<212> TYPE: DNA
<213> ORGANISM: Artificial Sequence
<220> FEATURE:
<223> OTHER INFORMATION: phaJ H1 Fp primer

<400> SEQUENCE: 47
gctgggccgc cgaagtgagc ttcgacggcg tcttcgttcc                             40

<210> SEQ ID NO 48
<211> LENGTH: 38
<212> TYPE: DNA
<213> ORGANISM: Artificial Sequence
<220> FEATURE:
<223> OTHER INFORMATION: phaJ H1 Rp primer

<400> SEQUENCE: 48
cgagcggtgt ggaggcatct attcagtcag ggatgcct                               38

<210> SEQ ID NO 49
<211> LENGTH: 43
<212> TYPE: DNA
<213> ORGANISM: Artificial Sequence
<220> FEATURE:
<223> OTHER INFORMATION: phaJ H2 Fp primer

<400> SEQUENCE: 49
ctacaaataa ttttgtttaa ctgactgaat aggaagagca agc                         43

<210> SEQ ID NO 50
<211> LENGTH: 41
<212> TYPE: DNA

```
<213> ORGANISM: Artificial Sequence
<220> FEATURE:
<223> OTHER INFORMATION: phaJ H2 Rp primer

<400> SEQUENCE: 50
ccctgatttc cataaggcgc cgcacgccgc gcggtgacga c                    41

<210> SEQ ID NO 51
<211> LENGTH: 18
<212> TYPE: DNA
<213> ORGANISM: Artificial Sequence
<220> FEATURE:
<223> OTHER INFORMATION: phaJ Fp primer

<400> SEQUENCE: 51
ttcgtggtct cggccgat                                              18

<210> SEQ ID NO 52
<211> LENGTH: 19
<212> TYPE: DNA
<213> ORGANISM: Artificial Sequence
<220> FEATURE:
<223> OTHER INFORMATION: phaJ Rp primer

<400> SEQUENCE: 52
caaagtcact gggttcccg                                             19
```

ENGINEERED MICROORGANISMS EXPRESSING ACETOACETYL-COA REDUCTASE VARIANTS AND METHOD FOR IMPROVING THE YIELD OF PHA

CROSS-REFERENCE TO RELATED APPLICATIONS

This application is a national stage application filed under 35 U.S.C. § 371 of International Patent Application No. PCT/CN2022/101802, filed Jun. 28, 2022, which claims the benefit of CN202210353439.7 filed Apr. 6, 2022.

INCORPORATION OF MATERIAL OF ASCII TEXT SEQUENCE LISTING BY REFERENCE

The sequence listing submitted herewith as a text file named "CNKH1042US_SUBSTITUTE_SEQUENCE_LISTING" created on Apr. 10, 2023, which is 50,000 bytes in size, is hereby incorporated by reference in its entirety.

TECHNICAL FIELD

The present invention relates to the technical field of microorganisms and, specifically, to acetoacetyl-CoA reductase variants for improving the yield of polyhydroxyalkanoates and their coding genes, as well as to engineered microorganisms expressing acetoacetyl-CoA reductase variants and a method for improving the yield of PHA.

BACKGROUND ART

Polyhydroxyalkanoates (PHAs) are a class of renewable and degradable polymers with multi-material properties synthesized by microorganisms, which have a wide range of applications in the fields of medicine, materials and environmental protection.

Polyhydroxyalkanoates are widely found in microbial cells, mainly acting as carbon sources and energy storage carriers. According to different monomer types and polymerization modes, PHAs have a series of material properties with diversity from hard and brittle hard plastic to soft elastomer. Polyhydroxybutyrate (PHB), one of the PHAs, is a commercially useful complex biopolymer produced by bacteria with a variety of potential applications, including use as a biodegradable/thermoplastic material, a source of chiral centers for organic synthesis of certain antibiotics, and as a matrix for drug delivery and bone replacement. Poly (3-hydroxybutyrate-co-3-hydroxyhexanoate) (PHBHHx, abbreviated as PHBH), which is also a type of PHA, is present in the cytoplasm in the form of insoluble microspherical particles.

*Ralstonia eutropha* (also known as *Cupriavidus necator*) is an important model bacterium for the study of PHA synthesis, and is the most studied strain for PHB production. When carbon is in excess and nitrogen is deficient, the strains can accumulate PHB in large quantities; while when other intracellular carbon sources are metabolically active, PHB synthesis is compromised. At present, the synthesis pathway of PHB in *Ralstonia eutropha* has been elaborated clearly: acetoacetyl-CoA is synthesized from Acyl-CoA under the action of phaA (β-ketothiolase), and then synthesizes 3-hydroxybutyric acid by the action of phaB (acetoacetyl-CoA reductase). The fermentation production performance of strains is a key factor affecting PHA production, therefore, it is important to develop genes and strains that facilitate PHA synthesis and accumulation.

SUMMARY OF THE INVENTION

The purpose of the present invention is to provide an acetoacetyl-CoA reductase variant and its coding gene capable of increasing the yield of polyhydroxyalkanoates, and engineered microorganisms for the production of polyhydroxyalkanoates.

Specifically, the present invention provides the following technical solutions:

In a first aspect, the present invention provides an acetoacetyl-CoA reductase (PhaB) variant, the acetoacetyl-CoA reductase variant has one or more of the following mutations compared to the wild-type acetoacetyl-CoA reductase represented by SEQ ID NO. 31:

(1) mutation of valine at position 141 to isoleucine or leucine;
(2) mutation of methionine at position 12 to threonine, serine, alanine, leucine, lysine or isoleucine;
(3) mutation of isoleucine at position 194 to valine, leucine or methionine;
(4) mutation of glutamic acid at position 42 to lysine, glutamine, leucine, aspartic acid, proline, threonine, asparagine, or histidine; and
(5) mutation of phenylalanine at position 55 to valine, alanine or isoleucine.

The mutations present in the acetoacetyl-CoA reductase variant provided by the present invention compared to the wild-type acetoacetyl-CoA reductase represented by SEQ ID NO. 31 may contain any one of the mutations from (1) to (5) above, or any combination of two, three, four or five of the mutations involved in (1) to (5) above.

The present invention demonstrates experimentally that both the variant containing a single mutation site as described above and the variant containing a combination of any two, three, four or five mutation sites can significantly increase the biomass and PHA content of the strain, and thus significantly increase the yield of PHA.

In a second aspect, the present invention provides nucleic acid molecules encoding the acetoacetyl-CoA reductase variants described above.

Based on the amino acid sequence of the acetoacetyl-CoA reductase variant provided above and the codon rules, a person skilled in the art is able to obtain the nucleotide sequences of nucleic acid molecules encoding the acetoacetyl-CoA reductase variants described above, and the nucleotide sequences of nucleic acid molecules encoding the same amino acid sequence are not unique, but all nucleic acid molecules capable of encoding the acetoacetyl-CoA reductase variants are within the scope of protection of the present invention.

In some embodiments of the present invention, the nucleotide sequences of the nucleic acid molecules are represented by any one of SEQ ID NOs. 3-28.

In a third aspect, the present invention provides a biological material including a nucleic acid molecule as described above, the biological material being an expression cassette, a vector or a host cell.

In some embodiments of the present invention, the expression cassette containing the nucleic acid molecule described above is obtained by operably linking a promoter, the nucleic acid molecule encoding the acetoacetyl-CoA reductase variant described above, and a terminator. Depending on the need of expression and the upstream and downstream sequences of the expression cassette, the expression cassette may also not contain a terminator or may contain other transcription and translation regulatory elements such as enhancers.

In some embodiments of the present invention, the vectors containing the nucleic acid molecules described above are plasmid vectors, which include replication-competent vectors and non-replication-competent vectors. The vectors carrying the nucleic acid molecules described above are not limited to plasmid vectors, but may also be vectors such as phages, viruses, and the like.

In some embodiments of the present invention, cells of *Escherichia coli* and *Ralstonia eutropha* containing the above nucleic acid molecules, expression cassettes or vectors are provided, but the type of host cells is not limited to this, and can be any microbial cells or animal cells that can be used for protein expression.

In a fourth aspect, the present invention provides the use of an acetoacetyl-CoA reductase variant or its coding gene in improving the yield of PHA produced by engineered microorganisms, the acetoacetyl-CoA reductase variants have one or more of the following mutations compared to the wild-type acetoacetyl-CoA reductase represented by SEQ ID NO. 31:
  (1) mutation of valine at position 141 to isoleucine or leucine;
  (2) mutation of methionine at position 12 to threonine, serine, alanine, leucine, lysine or isoleucine;
  (3) mutation of isoleucine at position 194 to valine, leucine or methionine; (4) mutation of glutamic acid at position 42 to lysine, glutamine, leucine, aspartic acid, proline, threonine, asparagine, or histidine; and
  (5) mutation of phenylalanine at position 55 to valine, alanine or isoleucine.

In some embodiments of the present invention, the acetoacetyl-CoA reductase variant is any one of the follows: WP 018973707.1, MB11365550.1, WP 019621003.1, PZ088445.1, WP 188557499.1, WP 018954578.1, WP 109722486.1, HBR97190.1, RKZ34011.1, PC129794.1, WP 152128546.1, WP 043577352.1, WP 028534370.1, WP 163146383.1, WP 020559877.1, EEV22383.1, WP 054674877.1, WP 116473412.1, WP 062152427.1, WP 070469244.1, MBE0623823.1, WP 166570087.1, WP 187671963.1, WP 124635583.1, WP 175829488.1 and WP 041099832.1.

In some embodiments of the present invention, the nucleotide sequences of the coding genes are represented by any one of SEQ ID NOs. 3-28.

The above use can be achieved by any one or more of the following ways:
  (1) introducing a plasmid comprising a gene encoding an acetoacetyl-CoA reductase variant in the microorganism; and
  (2) inserting one or more copies of the gene encoding the acetoacetyl-CoA reductase variant into the genome.

In some embodiments of the present invention, the genomic in situ phaB gene of the microorganism is not inactivated.

In some embodiments of the present invention, the genomic in situ phaB gene of the microorganism is retained intact.

In the above use, the engineered microorganism further includes one or more of the following modifications:
  (1) expression of a PHA polymerase variant capable of synthesizing PHBH;
  (2) enhanced expression and/or enzyme activity of (R)-enoyl-CoA hydratase.

In some embodiments of the present invention, the PHA polymerase variant capable of synthesizing PHBH contains a mutation of asparagine to serine at position 149 and a mutation of aspartate to glycine at position 171 compared to the original PHA polymerase.

In some embodiments of the present invention, the amino acid sequence of the PHA polymerase variant is represented by SEQ ID NO. 29.

In some embodiments of the present invention, the enhanced expression and/or enzyme activity of (R)-enoyl-CoA hydratase is achieved by initiating the transcription of the gene encoding (R)-enoyl-CoA hydratase in the genome with the promoter represented by SEQ ID NO. 30.

In the above use, the microorganism is preferably *Ralstonia eutropha*, *E. coli* or *Halomonas*.

In some embodiments of the present invention, the increase in the yield of PHA produced by the engineered microorganism is an increase in the yield of PHA produced by the engineered microorganism using lipids as carbon sources.

In some embodiments of the present invention, the increase in the yield of PHA produced by the engineered microorganism is an increase in the yield of PHA produced by the engineered microorganism using vegetable oils as carbon sources.

The vegetable oils include a mixture selected from one or more of palm oil, peanut oil, soybean oil, flax oil, rapeseed oil, castor oil, and corn oil.

In a fifth aspect, the present invention provides the use of an acetoacetyl-CoA reductase variant or its coding gene or the biological material containing the coding gene in the construction of microorganisms for the production of polyhydroxyalkanoates or their derivatives.

Based on the function that the acetoacetyl-CoA reductase variants provided by the present invention can increase the PHA production by microorganisms, nucleic acid molecules encoding these variants and biological materials containing these nucleic acid molecules can be used in the construction of strains for the production of PHA or derivatives thereof.

In the present invention, a derivative of PHA is a metabolite synthesized using PHA as a precursor substance. In the case of increased PHA synthesis capacity, the yield of metabolites synthesized with PHA as a precursor can usually be increased accordingly.

In the above use, the microorganism is preferably *Ralstonia eutropha*, *E. coli* or *Halomonas*.

In some embodiments of the present invention, the nucleic acid molecule represented by any one of SEQ ID NOs. 3-28 is introduced into *Ralstonia eutropha* to construct a PHA producing strain.

In a sixth aspect, the present invention provides an engineered *Ralstonia eutropha*, the engineered *Ralstonia eutropha* expresses the acetoacetyl-CoA reductase variant.

Compared with the wild-type acetoacetyl-CoA reductase represented by SEQ ID NO. 31, the acetoacetyl-CoA reductase variant has one or more of the following mutations:
  (1) mutation of valine at position 141 to isoleucine or leucine;
  (2) mutation of methionine at position 12 to threonine, serine, alanine, leucine, lysine or isoleucine;
  (3) mutation of isoleucine at position 194 to valine, leucine or methionine;
  (4) mutation of glutamic acid at position 42 to lysine, glutamine, leucine, aspartic acid, proline, threonine, asparagine, or histidine; and (5) mutation of phenylalanine at position 55 to valine, alanine or isoleucine.

In some embodiments of the present invention, the acetoacetyl-CoA reductase variant is any one of the follows: WP 018973707.1, MB11365550.1, WP 019621003.1, PZ088445.1, WP 188557499.1, WP 018954578.1, WP 109722486.1, HBR97190.1, RKZ34011.1, PC129794.1, WP 152128546.1, WP 043577352.1, WP 028534370.1, WP 163146383.1, WP 020559877.1, EEV22383.1, WP 054674877.1, WP 116473412.1, WP 062152427.1, WP 070469244.1, MBE0623823.1, WP 166570087.1, WP 187671963.1, WP 124635583.1, WP 175829488.1 and WP 041099832.1.

In the present invention, expression of the target enzyme or a variant thereof may be achieved by any one or more of the following methods:
(1) introducing a plasmid comprising a gene encoding the acetoacetyl-CoA reductase variant; and
(2) inserting one or more copies of the gene encoding the acetoacetyl-CoA reductase variant into the genome.

In some embodiments of the present invention, the acetoacetyl-CoA reductase variant is expressed by inserting one copy of the gene encoding the acetoacetyl-CoA reductase variant into the genome.

In some embodiments of the present invention, the gene encoding the acetoacetyl-CoA reductase variant is inserted in the genome at a location downstream of the coding region of the phaC gene or its coding region.

In some embodiments of the present invention, the gene encoding the acetoacetyl-CoA reductase variant is represented by any one of SEQ ID NOs. 3-28. The sequences of these coding genes are those obtained according to the codon preference of *Ralstonia eutropha* and combined with manual optimization and screening to enable efficient and correct expression of the acetoacetyl-CoA reductase variant in *Ralstonia eutropha*, the use of which facilitates the acetoacetyl-CoA reductase variant to play a better role in improving PHA synthesis in *Ralstonia eutropha*.

In some embodiments of the present invention, the genomic in situ phaB gene of the microorganism is not inactivated.

In some embodiments of the present invention, the genomic in situ phaB gene of the microorganism is retained intact.

In some embodiments of the present invention, the engineered *Ralstonia eutropha* for synthesis of PHBH is provided, and to facilitate synthesis of PHBH, the engineered *Ralstonia eutropha* further comprises one or more of the following modifications:
(1) expression of a PHA polymerase variant capable of synthesizing PHBH; and
(2) enhanced expression and/or enzyme activity of (R)-enoyl-CoA hydratase.

Wherein, the PHA polymerase variant capable of synthesizing PHBH can be obtained by mutating the amino acid sequence of the bacterial PHA polymerase to enable it to polymerize C6 fatty acid (3-hydroxyhexanoic acid), either by using a prior art PHA polymerase variant capable of polymerizing C6 fatty acid (3-hydroxyhexanoic acid), or by combining the mutation sites of prior art PHA polymerase variants capable of polymerizing PHBH to obtain new and more efficient PHA polymerase variants.

In some embodiments of the present invention, the PHA polymerase variant capable of synthesizing PHBH contains a mutation of asparagine to serine at position 149 and a mutation of aspartic acid to glycine at position 171 compared to the original PHA polymerase.

In some embodiments of the present invention, the amino acid sequence of the PHA polymerase variant is represented by SEQ ID NO. 29.

The above expression of a PHA polymerase variant capable of synthesizing PHBH is achieved by any one or more of the following ways:
(1) introducing a plasmid comprising a gene encoding the PHA polymerase variant capable of synthesizing PHBH; and
(2) inserting one or more copies of the gene encoding the PHA polymerase variant capable of synthesizing PHBH into the genome.

In some embodiments of the present invention, expression of the PHA polymerase variant capable of synthesizing PHBH is accompanied by inactivation of the original PHA polymerase coding gene of the genome.

In some embodiments of the present invention, the gene encoding the PHA polymerase variant capable of synthesizing PHBH is inserted into the genome.

In some embodiments of the present invention, an expression plasmid containing the gene encoding a variant of PHA polymerase capable of synthesizing PHBH is introduced.

In some embodiments of the present invention, the expression plasmid is a stable expression plasmid and stable expression of the plasmid is achieved by carrying in the plasmid a synthetic gene for a metabolite essential for the growth of the strain while inactivating the synthetic gene in the genome.

In some embodiments of the present invention, the plasmid containing the gene encoding the PHA polymerase variant represented by SEQ ID NO. 29 further contains the proC gene and the genomic proC gene of the engineered *Ralstonia eutropha* is inactivated.

The above-mentioned enhancement of expression of the enzyme may be achieved by any one or more of the following ways (1)-(4):
(1) introducing a vector containing a gene encoding the enzyme;
(2) increasing the copy number of the gene encoding the enzyme in the genome;
(3) altering the sequence of transcription and/or translation regulatory elements (including promoters, and the like) of a gene encoding the enzyme in the genome; and
(4) altering the nucleotide sequence of the gene encoding the enzyme.

The enhancement of the enzyme activity may be achieved by substitution, deletion or insertion of one or more amino acids of the enzyme.

In some embodiments of the present invention, the enhanced expression and/or enzyme activity of (R)-enoyl-CoA hydratase is achieved by initiating the transcription of the gene encoding (R)-enoyl-CoA hydratase in the genome with the promoter represented by SEQ ID NO. 30.

In some embodiments of the present invention, initiation of transcription of the gene encoding (R)-enoyl-CoA hydratase in the genome with the promoter represented by SEQ ID NO. 30 is achieved by inserting the promoter represented by SEQ ID NO. 30 in the intergenic region of the gene encoding genomic (R)-enoyl-CoA hydratase and its upstream gene.

In some embodiments of the present invention, the engineered *Ralstonia eutropha* is obtained by modification with wild-type *Ralstonia eutropha*, *Ralstonia eutropha* strain H16 or *Ralstonia eutropha* BPS-050 as the original strain.

Among them, *Ralstonia eutropha* BPS-050 has been deposited in China General Microbiological Culture Collection Center (CGMCC for short, Address: Building 3, NO. 1

Courtyard, West Beichen Road, Chaoyang District, Beijing, Institute of Microbiology, Chinese Academy of Sciences, postal code: 100101) on Oct. 13, 2021, with the taxonomic designation of *Ralstonia eutropha*, a deposit number of CGMCC No. 23600.

The present invention has experimentally confirmed that expression of the acetoacetyl-CoA reductase variant provided by the present invention in the above original strain can significantly improve the yield of PHA.

In a seventh aspect, the present invention provides a library of engineered *Ralstonia eutropha* transformants, the library of transformants includes at least 2 strains of the engineered *Ralstonia eutropha* described above.

In some embodiments of the present invention, the transformant library of engineered *Ralstonia eutropha* expresses any one of the following acetoacetyl-CoA reductase variants selected from the group consisting of: WP 018973707.1, MBI1365550.1, WP 019621003.1, PZ088445.1, WP 188557499.1, WP 018954578.1, WP 109722486.1, HBR97190.1, RKZ34011.1, PC129794.1, WP 152128546.1, WP 043577352.1, WP 028534370.1, WP 163146383.1, WP 020559877.1, EEV22383.1, WP 054674877.1, WP 116473412.1, WP 062152427.1, WP 070469244.1, MBE0623823.1, WP 166570087.1, WP 187671963.1, WP 124635583.1, WP 175829488.1 and WP 041099832.1, the amino acid sequences of the acetoacetyl-CoA reductase variants expressed by each strain of the engineered *Ralstonia eutropha* in the transformant library are different.

In some embodiments of the present invention, the library of transformants includes any 2 to 26 strains of the engineered *Ralstonia eutropha* described above.

In an eighth aspect, the present invention provides a method of constructing the engineered *Ralstonia eutropha*, which includes the step of modifying the *Ralstonia eutropha* to express the acetoacetyl-CoA reductase variant.

In some embodiments of the present invention, in order to promote the ability of engineered *Ralstonia eutropha* to synthesize PHBH, the method further includes one or more of the following modifications to *Ralstonia eutropha*:
(1) expression of a PHA polymerase variant capable of synthesizing PHBH; and
(2) enhanced expression and/or enzyme activity of (R)-enoyl-CoA hydratase.

In some embodiments of the present invention, the amino acid sequence of the PHA polymerase variant capable of synthesizing PHBH is represented by SEQ ID NO. 29.

In some embodiments of the present invention, the method includes initiating the transcription of the gene encoding the genomic (R)-enoyl-CoA hydratase with the promoter represented by SEQ ID NO. 30.

In some embodiments of the present invention, the method includes inserting into the genome the gene encoding the PHA polymerase variant capable of synthesizing PHBH.

In some embodiments of the present invention, the method includes introducing a plasmid carrying the gene encoding the PHA polymerase variant capable of synthesizing PHBH.

In some embodiments of the present invention, the method includes introducing a plasmid carrying the gene encoding the PHA polymerase variant capable of synthesizing PHBH and a proC gene, and inactivating the proC gene in the genome.

Wherein, gene inactivation can be achieved by gene knockout, silent expression, RNA interference and the like.

In a ninth aspect, the present invention provides any of the following uses of the engineered *Ralstonia eutropha*:

(1) usein the fermentation production of polyhydroxyalkanoates or their derivatives; and
(2) usein breeding strains for the fermentation production of polyhydroxyalkanoates or their derivatives.

In the present invention, polyhydroxyalkanoate (PHA) includes, but is not limited to, polyhydroxybutyrate (PHB), 3-hydroxybutyrate-co-3-hydroxyhexanoate (PHBHHx, or PHBH for short) and copolymers of 3-hydroxybutyrate and 3-hydroxyvalerate (PHBV), and the like.

In the above uses, the breeding of strains for fermentation production of polyhydroxyalkanoates or their derivatives may specifically be as follows: using the engineered *Ralstonia eutropha* provided by the present invention as the original strain, and breeding the strains for fermentation production of polyhydroxy fatty acid esters or their derivatives by genetic engineering modification, mutagenesis or domestication methods.

In a tenth aspect, the present invention provides a method for fermentative production of polyhydroxy fatty acid esters or derivatives thereof, which includes the step of culturing the engineered *Ralstonia eutropha* and obtaining a culture.

In some embodiments of the present invention, the method includes the following steps: activating and culturing the engineered *Ralstonia eutropha*, inoculating the activated bacteria into a seed medium for seed culture to obtain a seed solution, and then inoculating the seed solution into a production medium to obtain the culture.

The medium commonly used for the culture of *Ralstonia eutropha* can be selected for the above culture. The medium may contain carbon source, nitrogen source and inorganic salt. Among them, the carbon source includes, but is not limited to, a combination of one or more of vegetable oils (e.g. palm oil), sucrose, glucose, molasses, maltose, fructose, and arabinose; the nitrogen source includes, but is not limited to, a combination of one or more of corn syrup, yeast extract, urea, ammonium sulfate, ammonium chloride, ammonium nitrate, and potassium nitrate; the inorganic salt includes, but is not limited to, phosphate, potassium salt, sodium salt, magnesium salt, zinc salt, iron salt, manganese salt, calcium salt, borate, cobalt salt, copper salt, nickel salt and molybdenum salt.

In some embodiments of the present invention, the method further includes the step of separating and extracting the culture obtained from the culturing to collect the polyhydroxy fatty acid esters or their derivatives.

In an eleventh aspect, the present invention provides a method for increasing the yield of PHA produced by an engineered microorganism, the method including: modifying a *Ralstonia eutropha* to express an acetoacetyl-CoA reductase variant.

Compared with the wild-type acetoacetyl-CoA reductase represented by SEQ ID NO. 31, the acetoacetyl-CoA reductase variant has one or more of the following mutations:
(1) mutation of valine at position 141 to isoleucine or leucine;
(2) mutation of methionine at position 12 to threonine, serine, alanine, leucine, lysine or isoleucine;
(3) mutation of isoleucine at position 194 to valine, leucine or methionine;
(4) mutation of glutamic acid at position 42 to lysine, glutamine, leucine, aspartic acid, proline, threonine, asparagine, or histidine; and
(5) mutation of phenylalanine at position 55 to valine, alanine or isoleucine.

In some embodiments of the present invention, the acetoacetyl-CoA reductase variant is any one of the follows:

WP 018973707.1, MB11365550.1, WP 019621003.1, PZ088445.1, WP 188557499.1, WP 018954578.1, WP 109722486.1, HBR97190.1, RKZ34011.1, PC129794.1, WP 152128546.1, WP 043577352.1, WP 028534370.1, WP 163146383.1, WP 020559877.1, EEV22383.1, WP 054674877.1, WP 116473412.1, WP 062152427.1, WP 070469244.1, MBE0623823.1, WP 166570087.1, WP 187671963.1, WP 124635583.1, WP 175829488.1 and WP 041099832.1.

The expression in the method described above is achieved by any one or more of the following ways:
(1) introducing a plasmid comprising a gene encoding the acetoacetyl-CoA reductase variant; and
(2) inserting one or more copies of the gene encoding the acetoacetyl-CoA reductase variant into the genome.

In some embodiments of the present invention, the genomic in situ phaB gene of the microorganism is not inactivated.

In some embodiments of the present invention, the genomic in situ phaB gene of the microorganism is retained intact.

In some embodiments of the present invention, the nucleotide sequence of the coding gene is represented by any one of SEQ ID NOs. 3-28.

In the above use, the engineered microorganism further comprises one or more of the following modifications:
(1) expression of a PHA polymerase variant capable of synthesizing PHBH; and
(2) enhanced expression and/or enzyme activity of (R)-enoyl-CoA hydratase.

In some embodiments of the present invention, the PHA polymerase variant capable of synthesizing PHBH contains a mutation of asparagine to serine at position 149 and a mutation of aspartate to glycine at position 171 compared to the original PHA polymerase.

In some embodiments of the present invention, the amino acid sequence of the PHA polymerase variant is represented by SEQ ID NO. 29.

In some embodiments of the present invention, the enhanced expression and/or enzyme activity of (R)-enoyl-CoA hydratase is achieved by initiating the transcription of the gene encoding (R)-enoyl-CoA hydratase in the genome with the promoter represented by SEQ ID NO. 30. In some embodiments of the present invention, the method for enhancing the yield of PHA produced by engineered microorganisms is a method for enhancing the yield of PHA produced by engineered microorganisms using lipids as carbon sources.

In some embodiments of the present invention, the method for increasing the yield of PHA produced by engineered microorganisms is a method for increasing the yield of PHA produced by engineered microorganisms using vegetable oils as carbon sources.

The vegetable oils include a mixture selected from one or more of palm oil, peanut oil, soybean oil, flax oil, rapeseed oil, castor oil, and corn oil.

The beneficial effect of the present invention is that the acetoacetyl-CoA reductase variants and their coding genes provided by the present invention can significantly promote the synthesis and accumulation of PHA of the strain, and also promote the biomass increase of the strain, which in turn significantly improves the yield of PHA; the cell dry weight and PHA yield of the engineered *Ralstonia eutropha* constructed using the acetoacetyl-CoA reductase variant and its coding gene provided by the present invention are significantly increased, which provides new genes and strain resources for the development of engineered strains of PHA and has important application value for improving the fermentation production efficiency and reducing the production cost of PHA.

Specific Modes for Carrying Out the Embodiments

The application of the present invention is not limited to the embodiments described or exemplified in the specification below. The present invention can be used in other embodiments and may be implemented or carried out in a variety of ways. In addition, the phrases and terms used herein are for descriptive purposes and should not be regarded as limitation. As used herein, the words "include", "comprise", or "have", "contain", "relate to" and variations thereof are intended to include the items enumerated below and their equivalents, as well as other items.

The specific embodiments provided by the present invention are based in part or in whole on the following findings: the present invention found the acetoacetyl-CoA reductase variants and their coding genes that can significantly increase the yield of PHA produced by the strain. The genes encoding these acetoacetyl-CoA reductase variants can be introduced into strains having other genes required for PHA synthesis and used to increase the yield of PHA produced by these strains, resulting in engineered microorganisms. These engineered microorganisms can be used to produce PHA, and thereby improving the fermentation production performance of existing PHA fermentation production strains. Also, the engineered microorganisms can be subjected to other modifications on the basis of expression of the acetoacetyl-CoA reductase variant provided by the present invention. The present invention found that the expression of the acetoacetyl-CoA reductase variant can be modified at least in combination with the expression of the PHA polymerase (phaC) variant, and the enhanced expression of phaJ, to allow further improvement of PHA production.

In some embodiments, the present invention provides acetoacetyl-CoA reductase variants having one or more of the following mutations compared to the wild-type acetoacetyl-CoA reductase represented by SEQ ID NO. 31:
(1) mutation of valine at position 141 to isoleucine or leucine;
(2) mutation of methionine at position 12 to threonine, serine, alanine, leucine, lysine or isoleucine;
(3) mutation of isoleucine at position 194 to valine, leucine or methionine;
(4) mutation of glutamic acid at position 42 to lysine, glutamine, leucine, aspartic acid, proline, threonine, asparagine, or histidine; and
(5) mutation of phenylalanine at position 55 to valine, alanine or isoleucine.

Subject to the conditions of having any one or more of the mutations shown in (1) to (5) above, the present invention provides acetoacetyl-CoA reductase variants having the identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% or in the range consisting of any two of the preceding values with the amino acid sequence of any one of the following proteins: WP 018973707.1, MB11365550.1, WP 019621003.1, PZ088445.1, WP 188557499.1, WP 018954578.1, WP 109722486.1, HBR97190.1, RKZ34011.1, PC129794.1, WP 152128546.1, WP 043577352.1, WP 028534370.1, WP 163146383.1, WP 020559877.1, EEV22383.1, WP 054674877.1, WP 116473412.1, WP 062152427.1, WP 070469244.1, MBE0623823.1, WP 166570087.1, WP 187671963.1, WP 124635583.1, WP 175829488.1, WP 041099832.1.

The acetoacetyl-CoA reductase variant can include all acetoacetyl-CoA reductase variants having catalytic acetoacetyl-CoA activity to produce 3-hydroxybutyric acid, such as full-length acetoacetyl-CoA reductase, fragments of acetoacetyl-CoA reductase, truncated acetoacetyl-CoA reductase, and the like.

In some embodiments, the present invention provides genes encoding the acetoacetyl-CoA reductase variants described above that have the nucleotide sequences represented by any one of SEQ ID NOs. 3-28. These genes are optimized for expression in Ralstonia eutropha.

The above-mentioned acetoacetyl-CoA reductase variants and their coding genes provided by the present invention are capable of increasing the dry weight as well as the PHA content of the strain significantly, and thus effectively increasing the PHA production of the strain.

In some embodiments, the present invention provides engineered Ralstonia eutropha with the gene encoding the above acetoacetyl-CoA reductase variant inserted in the genome.

In some embodiments, the present invention provides engineered Ralstonia eutropha with the gene encoding the above-mentioned acetoacetyl-CoA reductase variant inserted in the genome of Ralstonia eutropha strain BPS-050. These engineered Ralstonia eutrophas have significantly higher PHA production than Ralstonia eutropha strain BPS-050.

In some embodiments, the present invention provides engineered Ralstonia eutropha with the gene encoding the acetoacetyl-CoA reductase variant described above inserted at the position where phaC is deleted in the genome of Ralstonia eutropha strain BPS-050.

In some embodiments, the present invention provides an engineered Ralstonia eutropha with the gene encoding the acetoacetyl-CoA reductase variant described above inserted into the genome of strain H16 of Ralstonia eutropha. These engineered Ralstonia eutrophas have a high PHB production.

In some embodiments, the present invention provides an engineered Ralstonia eutropha with the gene encoding the acetoacetyl-CoA reductase variant described above inserted at the phaC gene in the genome of Ralstonia eutropha strain H16.

In some embodiments, the present invention provides an engineered Ralstonia eutropha that the phaC gene in the genome of Ralstonia eutropha strain H16 is replaced with a gene encoding a PHA polymerase variant (the sequence of which is represented by SEQ ID NO. 29), the transcription of its genomic phaJ gene is initiated with a promoter represented by SEQ ID NO. 30, and the gene encoding the above-mentioned acetoacetyl-CoA reductase variant is inserted in its genome. These engineered Ralstonia eutrophas have significantly increased PHBH production.

Under the same fermentation culture conditions, the yield of polyhydroxyalkanoates of the engineered Ralstonia eutropha in the above embodiments was significantly higher than that of the original strain.

The following Examples are used to illustrate the present invention but are not intended to limit the scope of the present invention.

EXAMPLE 1: CONSTRUCTION OF A LIBRARY OF TRANSFORMANTS EXPRESSING ACETOACETYL-COA REDUCTASE VARIANTS AND SCREENING OF THE ACETOACETYL-COA REDUCTASE VARIANTS

In the present Example, Ralstonia eutropha BPS-050 was used as an original bacterium to construct a library of transformants containing different acetoacetyl-CoA reductase variants, specifically including the following steps:

Step 1: Construction of Basic Plasmids

PCR amplification was performed using the genome of Ralstonia eutropha as a template to obtain the phaC upstream and downstream homologous fragments phaC-H1 and phaC-H2, and the BsaI sites were added to the posterior and anterior ends of phaC-H1 and phaC-H2 to facilitate subsequent operations; the modified plasmid pK18mob (Orita, I., Iwazawa, et al. J. Biosci. Bioeng. 113, 63-69) was used as a template for PCR amplification to obtain the vector fragments, and the primer sequences used were shown in Table 1. The phaC-H1 and phaC-H2 were ligated to the vector fragment by Gibson Assembly method to obtain the recombinant plasmid pKO-C (sequence as represented by SEQ ID NO. 1).

TABLE 1

| Primer name | Primer sequence (5'-3') |
|---|---|
| pK-R | gcagacttggccgggtacca (SEQ ID NO: 32) |
| pK-F | cACCGCTCGTCACATCCTG (SEQ ID NO: 33) |
| phaCH1-F | tggtacccggccaagtctgcgggcgtgcccatgatgt aga (SEQ ID NO: 34) |
| phaCH1-R | TGAGACCCAAGGTCTCCATgatttgattgtctctctg ccgtc (SEQ ID NO: 35) |
| phaCH2-F | GGAGACCTTGGGTCTCAGTGACGCTTGCATGAGTGCC G (SEQ ID NO: 36) |
| phaCH2-R | CAGGATGTGACGAGCGGTGcatggtgtcgaccagctt gg (SEQ ID NO: 37) |

Step 2: Gene Synthesis

The genes encoding the different acetoacetyl-CoA reductase variants to be screened were sequenced separately to enable their better expression in Ralstonia eutropha. The optimized genes encoding the acetoacetyl-CoA reductase variants were synthesized separately by adding GGTCTCATC upstream and GTGAAGAGACC (SEQ ID NO: 38) downstream to the synthesized DNA sequences for subsequent operations.

Step 3: Construction of a Target Strain Containing a Target Gene

The plasmid pKO-C constructed in step 1 was assembled with the plasmid containing the optimized gene encoding the acetoacetyl-CoA reductase variant obtained by gene synthesis using Goldengate method to obtain recombinant plasmids pKO-C-N carrying different genes encoding acetoacetyl-CoA reductase variants, respectively (N stands for the loaded gene encoding the acetoacetyl-CoA reductase variant). Each plasmid was transferred into E. coli S17-1 and then into Ralstonia eutropha BPS-050 by conjugative transfer, and positive clones were screened with LB plates containing both 500 μg/mL spectinomycin and 100 μg/mL apramycin, taking advantage of the inability of the suicide plasmids to replicate in the host bacteria. The recombinant plasmids with homologous fragments in the positive clone were integrated at the specific positions in the genome where phaC-H1 and phaC-H2 are located, resulting in the first homologous recombinant bacterium. The first homologous recombinant bacterium was cultured on LB plates containing 100 mg/mL sucrose, and from these monoclonal clones, those without spectinomycin resistance were screened and PCR was performed using primers FphaCH1-F:

tggtctggctggcggactgag (SEQ ID NO: 39) and phaCH2-R: ggcgaactcatcctgcgcctc (SEQ ID NO: 40). The recombinant bacteria inserted with the target gene were identified by sequencing, and the recombinant bacteria obtained were the stable plasmid version of *Ralstonia eutropha* ReApro-CAphaC::N. A total of 221 transformants were obtained.

Step 4: Construction of Recombinant Bacteria Overexpressing the Original phaB Gene of *Ralstonia eutropha*

Referring to the method for constructing recombinant plasmids in step 3, recombinant plasmids containing the original phaB gene of *Ralstonia eutropha* were constructed using Gibson assembly as follows:

PCR amplification was performed using the plasmid obtained in step 1 as a template to obtain the plasmid backbone fragment. The phaB gene fragment was obtained by amplification using the genome of *Ralstonia eutropha* BPS-050 as a template. The above two fragments were ligated by Gibson Assembly method to obtain the recombinant plasmid pKO-C-phaB. The primers used in the construction process are represented by Table 2.

TABLE 2

| Primer name | Primer sequence |
|---|---|
| PKCH-CR | catGAtttgattgtctctctgccg (SEQ ID NO: 41) |
| pKCH-CF | GTGACGCTTGCATGAGTGCC (SEQ ID NO: 42) |
| phaB F | agagagacaatcaaaTCatgactcagcgcattgcgt atg (SEQ ID NO: 43) |
| phaB R | GGCACTCATGCAAGCGTCACtcagcccatatgcagg ccgc (SEQ ID NO: 44) |

The pKO-C-phaB plasmid was transferred into *E. coli* S17-1, and the recombinant bacterium was constructed with reference to the method in step 3 above, resulting in the overexpression strain ReAphaC::phaB that integrates the phaB gene at the phaC gene of the genome of *Ralstonia eutropha*.

Step 5: Screening for Acetoacetyl-CoA Reductase Variants that can Significantly Improve the PHA Yield of *Ralstonia eutropha*

(1) Fermentation Culture of Recombinant Bacteria Expressing Different Acetoacetyl-Coa Reductase Variants The recombinant bacteria expressing different acetoacetyl-CoA reductase variants obtained in step 3 were streaked on the plate to obtain single clones, the resulted single clones were inoculated in seed medium (4 mL) and cultured for 12 hours. The overnight culture was transferred to a 100 mL glass conical flask containing 10 mL LB medium for activation, inoculated with a final OD of about 0.1, cultured at 30° C., 220 rpm for 8 h, and then transfer culture can be carried out. The culture for PHA fermentation production was as follows: the pre-culture seed with an OD value between 6 and 7 was inoculated into a 250 mL shake flask containing 30 mL fermentation medium at an OD value of 0.1, then a certain amount of emulsifier was added, and after 48 h, the fermentation was stopped and the fermentation broth was centrifuged to obtain the bacteria. The bacteria were dried to a constant weight.

The formula of the above fermentation medium was as follows: 10% palm oil, 1 g/L $NH_4Cl$, 10 mL/L trace element solution I and 1 mL/L trace element solution II; wherein the composition of trace element solution I includes 20 g/L $MgSO_4$ and 2 g/L $CaCl_2$). The composition of trace element solution II includes 100 mg/L $ZnSO_4 \cdot 7H_2O$, 30 mg/L $MnCl_2 \cdot 4H_2O$, 300 mg/L $H_3BO_3$, 200 mg/L $CoCl_2 \cdot 6H_2O$, 10 mg/L $CuSO_4 \cdot 5H_2O$, 20 mg/L $NiCl_2 \cdot 6H_2O$ and 30 mg/L $NaMoO_4 \cdot 2H_2O$. The above reagents were all purchased from Sinopharm Chemical Reagent Co., Ltd.

(2) Detection of PHA Content

Preparation of esterification solution: 485 mL of anhydrous methanol was taken, 1 g/L of benzoic acid was added, and 15 mL of concentrated sulfuric acid was slowly added to prepare about 500 mL of esterification solution.

Sample preparation: after weighing the sample accurately, 2 mL of esterification solution and 2 mL of chloroform were added into the esterification tube. About 10 mg of PHA sample was weighed and treated in the same way as a standard sample. The esterification tube was sealed with a cap and reaction was performed at 100° C. for 4 hours. After the reaction was finished and the esterification tube was cooled to room temperature, 1 mL of deionized water was added, the resultant was subjected to vortex and shake until fully mixed, and allowed to stand for layering. After the water phase and the organic phase were completely separated, the lower organic phase was taken for gas chromatography (GC) analysis.

GC analysis of PHA composition and content: GC-2014 gas chromatograph from Shimadzu Company was used. The configuration of the chromatograph was as follows: HP-5 capillary column, hydrogen flame ionization detector (FID), SPL split inlet; high purity nitrogen as carrier gas, hydrogen as fuel gas, air as auxiliary gas; AOC-20S automatic sampler is used with acetone as washing liquid. The GC analysis program was set as follows: an inlet temperature of 240° C., a detector temperature of 250° C., an initial column temperature of 80° C., and a maintaining time of 1.5 minutes; rising to 140° C. at a rate of 30° C./min and maintaining for 0 min; rising to 240° C. at a rate of 40° C./min and maintaining for 2 minutes; the total time is 8 minutes. The GC results were quantified by internal standard normalization method based on peak area to calculate the composition and content of PHA.

The PHA yield of recombinant bacteria expressing different acetoacetyl-CoA reductase variants was detected, and after screening, it was found that most of the acetoacetyl-CoA reductase variants could not significantly increase the PHA yield of *Ralstonia eutropha*, and even many acetoacetyl-CoA reductase variants made the PHA yield of *Ralstonia eutropha* decrease significantly (even to below 40%), and only 26 acetoacetyl-CoA reductase variants could significantly increase the PHA production of *Ralstonia eutropha* (PHA content reached more than 83%). The results of PHA production and cell dry weight (CDW) of recombinant bacteria expressing these 26 acetoacetyl-CoA reductase variants are shown in Table 3. The CDW of the control strain was 10.34 g/L, the percentage of PHA was 82.21% and the percentage of H was 8.15 mol %, using the original bacterium *Ralstonia eutropha* BPS-050 as the control strain.

TABLE 3

| Accession number of the acetoacetyl-CoA reductase variants | V141I | M12T | I194V | E42K | F55V | Cell Dry Weight (g/L) | PHA content (%) | H molar ratio (%) |
|---|---|---|---|---|---|---|---|---|
| WP018973707.1 | ✓ | ✓ | ✓ | ✓ | ✓ | 12.65 | 91.18% | 9.09% |
| MBI1365550.1 | ✓ | ✓ | L | ✓ | ✓ | 13.06 | 87.94% | 9.94% |
| WP 019621003.1 | L | S | ✓ | ✓ | ✓ | 11.86 | 83.64% | 9.45% |
| PZO88445.1 | ✓ | ✓ | M | ✓ | A | 11.52 | 84.82% | 9.02% |
| WP 188557499.1 | ✓ | ✓ | ✓ | Q | ✓ | 12.27 | 83.64% | 8.39% |
| WP 018954578.1 | ✓ | ✓ | ✓ | — | ✓ | 10.25 | 88.03% | 9.45% |
| WP 109722486.1 | ✓ | ✓ | ✓ | — | ✓ | 10.07 | 92.61% | 9.84% |
| HBR97190.1 | — | ✓ | ✓ | ✓ | I | 11.78 | 84.90% | 9.65% |
| RKZ34011.1 | L | ✓ | — | L | ✓ | 12.57 | 84.00% | 9.00% |
| PCI29794.1 | — | ✓ | ✓ | D | I | 12.73 | 83.00% | 9.00% |
| WP 152128546.1 | ✓ | A | — | ✓ | I | 12.04 | 83.59% | 9.15% |
| WP 043577352.1 | ✓ | — | ✓ | Q | I | 12.02 | 84.51% | 9.59% |
| WP 028534370.1 | ✓ | — | ✓ | D | A | 12.06 | 84.00% | 9.00% |
| WP 163146383.1 | ✓ | — | ✓ | ✓ | — | 11.81 | 86.93% | 7.96% |
| WP 020559877.1 | — | ✓ | — | ✓ | ✓ | 10.73 | 85.37% | 8.02% |
| EEV22383.1 | ✓ | L | ✓ | — | — | 13.18 | 83.32% | 8.97% |
| WP 054674877.1 | — | K | — | ✓ | ✓ | 12.09 | 84.12% | 12.84% |
| WP 116473412.1 | — | A | — | Q | I | 11.36 | 83.58% | 9.41% |
| WP 062152427.1 | — | ✓ | — | P | I | 12.14 | 85.75% | 9.83% |
| WP 070469244.1 | — | I | M | T | — | 12.06 | 83.62% | 9.83% |
| MBE0623823.1 | — | — | — | D | ✓ | 10.62 | 84.06% | 7.99% |
| WP 166570087.1 | ✓ | — | — | N | — | 12.03 | 87.40% | 7.94% |
| WP 187671963.1 | ✓ | — | — | N | — | 11.64 | 85.04% | 7.96% |
| WP 124635583.1 | — | ✓ | ✓ | Q | — | 12.89 | 84.00% | 8.00% |
| WP 175829488.1 | — | — | — | D | — | 12.41 | 84.00% | 9.00% |
| WP 041099832.1 | — | — | — | H | — | 12.81 | 83.27% | 9.05% |

Note:
In Table 3, "✓" represents that it contains the mutation site V141I, M12T, I194V, E42K and F55V, respectively; "—" represents that the amino acid at the position is not mutated; L, S, and the like represent mutation to other amino acid types such as leucine, serine and the like at the corresponding mutation site; PHA content (%) is the content of PHA in the bacteria; H molar ratio (%) is the molar percentage of H(3HHx) in PHBH (PHBHHx).

(3) Fermentation Culture and PHA Content Detection of Recombinant Bacteria Overexpressing the Original phaB The recombinant bacteria overexpressing the original phaB gene obtained in step 4 above were fermented and cultured according to the method in (1) above, and the PHA content was detected according to the method in (2) above, with the original bacterium *Ralstonia eutropha* BPS-050 as the control strain.

The fermentation results are shown in Table 4. The results showed that overexpression of the phaB gene of *Ralstonia eutropha* itself could not improve the yield of PHA.

TABLE 4

| | Control strain | phaB overexpression |
|---|---|---|
| Cell Dry weight (g/L) | 10.34 | 11.21 |
| H molar ratio (%) | 8.15% | 8.43% |
| Content of PHA (%) | 82.21% | 81.96% |

EXAMPLE 2: ANALYSIS OF CONSERVED SITES OF ACETOACETYL-COA REDUCTASE VARIANTS

The conserved sites of 26 acetoacetyl-CoA reductase variants (shown in Table 3) screened in Example 1 were analyzed, while 16 acetoacetyl-CoA reductase variants with PHA yield lower than 40% were randomly selected, and these acetoacetyl-CoA reductase variants were subjected to multiple-sequence alignment, and the results were analyzed by certain computer algorithms to finally determine the conserved sites of the acetoacetyl-CoA reductase variants that can effectively improve the production of PHA, which are: V141I, M12T, I194V, E42K and F55V, respectively, using the phaB gene of *Ralstonia eutropha* as the sequence reference.

EXAMPLE 3: CONSTRUCTION OF A LIBRARY OF TRANSFORMANTS EXPRESSING ACETOACETYL-COA REDUCTASE VARIANTS USING H16 AS AN ORIGINAL BACTERIUM AND THE PERFORMANCE VERIFICATION THEREOF

In the present Example, *Ralstonia eutropha* H16 was used as the original bacterium (the phaC gene of *Ralstonia eutropha* H16 strain was not mutated and the promoter of phaJ gene was not introduced upstream), and 26 acetoacetyl-CoA reductase variants obtained from the screening of Example 1 were expressed in *Ralstonia eutropha* H16, respectively.

The recombinant plasmids and recombinant bacteria were constructed by referring to Example 1 except that after inserting the gene encoding the acetoacetyl-CoA reductase variant into the phaC gene of the genome, the upstream primer phaCH1-F and the downstream primer phaCH1-R of the homologous fragments in Example 1 were accordingly changed to iphaCH1 F: tggtacccggccaagtctgtgtggaac-tacgtggtcgac (SEQ ID NO: 45); iphaCH1 R: TGAGACC-CAAGGTCTCCATtcatgccttggctttgacgtatc (SEQ ID NO: 46), and other operations were performed as in Example 1 to construct recombinant bacteria expressing the 26 acetoacetyl-CoA reductase variants obtained from the screening of Example 1, respectively.

The constructed recombinant bacteria were subjected to fermentation culture and PHA yield detection according to the method of Example 1, and the detection results of the cell dry weight and the PHA yield are shown in Table 5. The results showed that the 26 acetoacetyl-CoA reductase variants obtained from the screening of Example 1 were also able to increase the cell dry weight and PHA content of *Ralstonia eutropha* strain H16, thus effectively increasing the yield of PHA.

TABLE 5

|  | Cell Dry weight(g/L) | Content of PHA(%) |
|---|---|---|
| H16 (control strain) | 8.34 | 52.89% |
| WP 018973707.1 | 9.94 | 72.18% |
| MBI1365550.1 | 10.26 | 71.74% |
| WP 019621003.1 | 9.34 | 68.44% |
| PZO88445.1 | 9.42 | 72.82% |
| WP 188557499.1 | 10.10 | 67.94% |
| WP 018954578.1 | 9.46 | 69.13% |
| WP 109722486.1 | 9.14 | 71.21% |
| HBR97190.1 | 10.46 | 72.50% |
| RKZ34011.1 | 9.37 | 69.80% |
| PCI29794.1 | 9.70 | 66.50% |
| WP 152128546.1 | 9.18 | 66.49% |
| WP 043577352.1 | 9.07 | 68.51% |
| WP 028534370.1 | 10.07 | 67.40% |
| WP 163146383.1 | 9.65 | 66.73% |
| WP 020559877.1 | 9.03 | 68.77% |
| EEV22383.1 | 9.46 | 63.72% |
| WP 054674877.1 | 8.84 | 60.72% |
| WP 116473412.1 | 8.66 | 58.98% |
| WP 062152427.1 | 9.65 | 60.55% |
| WP 070469244.1 | 9.00 | 56.02% |
| MBE0623823.1 | 8.02 | 56.66% |
| WP 166570087.1 | 8.98 | 55.20% |
| WP 187671963.1 | 9.48 | 62.54% |
| WP 124635583.1 | 9.84 | 60.10% |
| WP 175829488.1 | 10.30 | 55.60% |
| WP 041099832.1 | 8.19 | 56.97% |

EXAMPLE 4: CONSTRUCTION OF A LIBRARY OF TRANSFORMANTS EXPRESSING ACETOACETYL-COA REDUCTASE VARIANTS USING A GENETICALLY MODIFIED BACTERIUM OF H16 AS AN ORIGINAL BACTERIUM AND THE PERFORMANCE VERIFICATION THEREOF

In the present Example, Ralston/a *eutropha* H16 was used as an original bacterium, and its genomic phaC gene was mutated into a phaC gene variant (the sequence of the coding protein is represented by SEQ ID NO. 29), and the promoter represented by SEQ ID NO. 30 was inserted upstream of the genomic phaJ gene, on the basis of which the 26 acetoacetyl-CoA reductase variants obtained from the screening of Example 1 were expressed, respectively. The specific method was as follows:

Step 1: Substitution of the Genomic phaC Gene of *Ralstonia eutropha*

The synthetic sequence of the phaC gene variant is represented by SEQ ID NO. 2, which contains about 600 bp fragment upstream and downstream of the phaC gene and the phaC mutant, and at the same time, GGTCTCATC was added upstream and GTGAAGAGACC (SEQ ID NO: 38) was added downstream of the synthetic sequence to facilitate subsequent ligation with the vector. The synthetic gene was ligated to the pKO-C vector fragment by the Goldengate method to obtain the recombinant plasmid pK18mob-ΔphaC::phaCac.

The recombinant plasmid pK18mob-ΔphaC::phaCac was transferred into *E. coli* S17-1 and then into *Ralstonia eutropha* H16 by conjugative transfer method, and the positive clones were screened with LB plates containing both 200 μg/mL kanamycin and 100 μg/mL apramycin, taking advantage of the inability of the suicide plasmids to replicate in the host bacteria. The recombinant plasmids with homologous fragments in the positive clone were integrated into the genome at the specific locations where H1 and H2 are located, resulting in the first homologous recombinant bacterium. The first homologous recombinant bacterium was cultured on LB plates containing 100 mg/mL sucrose by scratching single clones, and from these single clones, clones without kanamycin resistance were screened, and PCR was performed with primers phaC-H1 FP and phaC-H2 RP, and sequencing was performed to identify the recombinant bacteria with phaC gene substitution, and the recombinant bacterium obtained was *Ralstonia eutropha* ReΔphaC::phaCac.

Step 2: Construction of Recombinant Bacteria with Specific Promoter Inserted Upstream of phaJ4b Gene
(1) PCR amplification was performed using the genome of *Ralstonia eutropha* ReΔphaC::phaCac obtained in step 1 as a template, and the upstream homologous fragment H1 of the promoter of the phaJ gene was obtained using phaJ-H1 Fp and phaJ-H1 Rp; and the downstream homologous fragment H2 of the promoter of the phaJ gene was obtained using phaJ-H2 Fp and phaJ-H2 Rp.
(2) Gene synthesis of the promoter phaJ43 (SEQ ID NO. 30) of the phaJ gene
(3) The fragments of H1 and H2 obtained by PCR and the phaJ43 promoter were ligated to the vector fragment by Gibson Assembly method to obtain the recombinant plasmid pK18mob-phaJ43. The primers used above are shown in Table 6.

TABLE 6

| Primer name | Primer sequence (5'-3') |
|---|---|
| phaJ-H1 Fp | gctgggccgccgaagtgagcttcgacggcgtcttcg ttcc (SEQ ID NO: 47) |
| phaJ-H1 Rp | cgagcggtgtggaggcatctattcagtcagggatgc ct (SEQ ID NO: 48) |
| phaJ-H2 Fp | ctacaaataattttgtttaactgactgaataggaag agcaagc (SEQ ID NO: 49) |
| phaJ-H2 Rp | ccctgatttccataaggcgccgcacgccgcgcggtg acgac (SEQ ID NO: 50) |
| phaJ Fp | ttcgtggtctcggccgat (SEQ ID NO: 51) |
| phaJ Rp | Caaagtcactgggttcccg (SEQ ID NO: 52) |

(4) The recombinant plasmid pK18mob-phaJ43 was transferred into *E. coli* S17-1 and then into *Ralstonia eutropha* ReΔphaC::phaCac by conjugative transfer method, and the positive clones were screened with LB plates containing both 200 μg/mL kanamycin and 100 μg/mL apramycin, taking advantage of the inability of the suicide plasmids to replicate in the host bacterium. The positive clones with a homologous fragment of recombinant plasmid were integrated into the genome at the specific locations where H1 and H2 are located, resulting in the first homologous recombinant bacterium. The first homologous recombinant bacterium was grown on LB plates containing 100 mg/mL sucrose by scratching single clones, and from these single clones, clones without kanamycin resistance were screened and identified by PCR with primers phaJ Fp and phaJ Rp to identify recombinant bacteria of corresponding size, and the recombinant bacterium obtained was ReΔphaC::phaCac-phaJ43.

(5) Expression of 26 acetoacetyl-CoA reductase variants obtained from the screening of Example 1, respectively in *Ralstonia eutropha* ReΔphaC::phaCac_phaJ43 The recombinant plasmid and recombinant bacterium were constructed by referring to Example 1, and the recombinant bacterium ReΔphaC::phaCac_phaJ43 expressing each of the 26 acetoacetyl-CoA reductase variants screened in Example 1 was constructed.

The constructed recombinant bacteria were subjected to fermentation culture and PHA yield detection according to the method of Example 1. The results showed that the increase ratio of cell dry weight and PHA content of the recombinant bacteria expressing the acetoacetyl-CoA reductase variants are comparable to the control strain (recombinant bacteria ReΔphaC::phaCac_phaJ43, which did not express the acetoacetyl-CoA reductase variant in the present Example) as in Example 1. It is thus demonstrated that the 26 acetoacetyl-CoA reductase variants screened in Example 1 were also able to significantly increase the cell dry weight and PHA content, and thus the PHA yield, of strain ReΔphaC::phaCac_phaJ43 of *Ralstonia eutropha*.

EXAMPLE 5: FERMENTATION EXPERIMENT OF THE RECOMBINANT BACTERIA

The recombinant bacteria constructed in Examples 1, 3 and 4 above were subjected to fermentation experiments using other vegetable oils as carbon sources, i.e., replacing palm oil with soybean oil and flax oil in the fermentation media used in Examples 1, 3 and 4, respectively, other fermentation methods were the same as those in Example 1. The results showed that the cell dry weight and PHA yield of each recombinant bacterium when fermented with soybean oil or flax oil as the carbon source tended to be consistent with the results when palm oil was used as the carbon source, showing no significant differences. Although the present invention has been described exhaustively above with a general description and specific embodiments, some modifications or improvements can be made on the basis of the present invention, as will be apparent to a person skilled in the art. Therefore, these modifications or improvements made without departing from the spirit of the present invention are within the scope of protection claimed by the present invention.

INDUSTRIAL APPLICABILITY

The present invention provides engineered microorganisms expressing acetoacetyl-CoA reductase variants and their coding genes, uses of the acetoacetyl-CoA reductase variants and their coding genes in improving the yield of PHA produced by microorganisms, and a method for improving the yield of PHA produced by microorganisms. By expressing the acetoacetyl-CoA reductase variant in the microorganism, the PHA synthesis and accumulation capacity of the microorganism is significantly improved, and meanwhile, the biomass of the microorganism is promoted, and thus the yield of PHA is effectively improved. The acetoacetyl-CoA reductase variants, their coding genes and the engineered microorganisms provided by the present invention provide new genes and strain resources for the development of production strains of PHA, and have important economic value and application prospects for improving the fermentation production efficiency and reducing the production cost of PHA.

What is claimed is:

1. A method for engineering *Ralstonia eutropha* to produce polyhydroxyalkanoate from palm oil as a carbon source, wherein the method comprises a step of: modifying a *Ralstonia eutropha* cell to express a gene encoding an acetoacetyl-CoA reductase variant to produce an engineered *Ralstonia eutropha*; and
the acetoacetyl-CoA reductase variant comprises the amino acid sequence encoded by SEQ ID NO: 3.

2. The method according to claim 1, wherein the modification to express the CoA reductase variant is achieved by any one or more of the following ways:
   (1) introducing a plasmid comprising a gene encoding the acetoacetyl-CoA reductase variant; and
   (2) inserting one or more copies of a gene encoding the acetoacetyl-CoA reductase variant into the genome of the *Ralstonia eutropha*.

3. The method according to claim 2, wherein the method further comprises one or more of the following steps:
   (1) expressing a polyhydroxyalkanoate polymerase variant capable of synthesizing poly(3-hydroxybutyrate-co-3-hydroxyhexanoate) wherein the polyhydroxyalkanoate polymerase variant comprises the amino acid sequence of SEQ ID NO: 29; and
   (2) enhancing expression and/or enzyme activity of (R)-enoyl-CoA hydratase, the enhanced expression and/or enzyme activity of (R)-enoyl-CoA hydratase is achieved by initiating the transcription of a gene encoding (R)-enoyl-CoA hydratase in the *Ralstonia eutropha* genome with a promoter comprising the nucleotide sequence of SEQ ID NO: 30.

4. The method according to claim 1, wherein the method further comprises one or more of the following steps:
   (1) expressing a polyhydroxyalkanoate polymerase variant capable of synthesizing poly(3-hydroxybutyrate-co-3-hydroxyhexanoate) wherein the polyhydroxyalkanoate polymerase variant comprises the amino acid sequence of SEQ ID NO: 29; and
   (2) enhancing expression and/or enzyme activity of (R)-enoyl-CoA hydratase, the enhanced expression and/or enzyme activity of (R)-enoyl-CoA hydratase is achieved by initiating the transcription of a gene encoding (R)-enoyl-CoA hydratase in the *Ralstonia eutropha* genome with a promoter comprising the nucleotide sequence of SEQ ID NO: 30.

5. The method according to claim 1, wherein the method further comprises the following step:
   (1) expressing a polyhydroxyalkanoate polymerase variant capable of synthesizing poly(3-hydroxybutyrate-co-3-hydroxyhexanoate) wherein the polyhydroxyalkanoate polymerase variant comprises the amino acid sequence of SEQ ID NO: 29.

* * * * *